US 9,696,288 B2

(12) United States Patent
Kashima et al.

(10) Patent No.: US 9,696,288 B2
(45) Date of Patent: Jul. 4, 2017

(54) ATTACHED MATTER TESTING DEVICE AND TESTING METHOD

(71) Applicant: Hitachi, Ltd., Tokyo (JP)

(72) Inventors: Hideo Kashima, Tokyo (JP); Masakazu Sugaya, Tokyo (JP); Koichi Terada, Tokyo (JP); Yasunori Doi, Tokyo (JP); Yasutaka Suzuki, Tokyo (JP); Hisashi Nagano, Tokyo (JP); Yuichiro Hashimoto, Tokyo (JP); Yasuaki Takada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 54 days.

(21) Appl. No.: 14/349,672

(22) PCT Filed: Oct. 2, 2012

(86) PCT No.: PCT/JP2012/075459
§ 371 (c)(1),
(2) Date: Apr. 4, 2014

(87) PCT Pub. No.: WO2013/051530
PCT Pub. Date: Apr. 11, 2013

(65) Prior Publication Data
US 2014/0238106 A1    Aug. 28, 2014

(30) Foreign Application Priority Data

Oct. 6, 2011 (JP) ................... 2011-221847

(51) Int. Cl.
*G01N 1/26* (2006.01)
*G01N 33/00* (2006.01)
(Continued)

(52) U.S. Cl.
CPC ....... *G01N 33/0011* (2013.01); *G01N 1/2202* (2013.01); *G01N 2001/024* (2013.01); *G01N 2001/028* (2013.01)

(58) Field of Classification Search
CPC .............................................. G01N 2001/024
See application file for complete search history.

(56) References Cited

U.S. PATENT DOCUMENTS 3,612,067 A * 10/1971 Wallenborn ............. A24B 5/14
131/324
4,909,089 A    3/1990 Achter et al.
(Continued)

FOREIGN PATENT DOCUMENTS

CA        2018697      12/1990
JP        63-134933     6/1988
(Continued)

Primary Examiner — Laura Martin
Assistant Examiner — Alex Devito
(74) Attorney, Agent, or Firm — Baker Botts L.L.P.

(57) ABSTRACT

Provided is a technique to identify a sample substance attached to an inspection target easily and precisely, while improving the rate of operation and reducing the number of persons required for inspection. A trace detecting system includes detection means to detect the size (vertical and horizontal dimensions) of an inspection target, and selects an air nozzle capable of spraying air jet at 15 m/s or more to the surface of the inspection target for air jet spraying.

11 Claims, 25 Drawing Sheets

(51) Int. Cl.
*G01N 1/22* (2006.01)
*G01N 1/02* (2006.01)

(56) References Cited

U.S. PATENT DOCUMENTS

| | | | |
|---|---|---|---|
| 6,334,365 | B1 | 1/2002 | Linker et al. |
| 7,002,145 | B2 | 2/2006 | Ishikawa et al. |
| 8,217,339 | B2 | 7/2012 | Kashima et al. |
| 2011/0186436 | A1* | 8/2011 | Novosselov ........... B01D 15/08 204/600 |

FOREIGN PATENT DOCUMENTS

| | | |
|---|---|---|
| JP | 01-212849 | 8/1989 |
| JP | 02-198333 | 8/1990 |
| JP | 07-006729 | 1/1995 |
| JP | 8-33338 | 3/1996 |
| JP | 09-126965 | 5/1997 |
| JP | 2004-301749 | 10/2004 |
| JP | 2008-018355 | 1/2008 |
| JP | 2008-544836 | 12/2008 |
| JP | 2009-031315 | 2/2009 |
| JP | 2009-031316 | 2/2009 |
| JP | 4568327 | 8/2010 |
| JP | 4714257 | 4/2011 |
| JP | 5044530 | 7/2012 |
| JP | 2013-083472 | 5/2013 |
| JP | 2013-205013 | 10/2013 |
| JP | 2013-245948 | 12/2013 |
| WO | WO 91/09307 | 6/1991 |
| WO | WO 2006/124500 | 11/2006 |
| WO | WO 2012/063796 | 5/2012 |

* cited by examiner

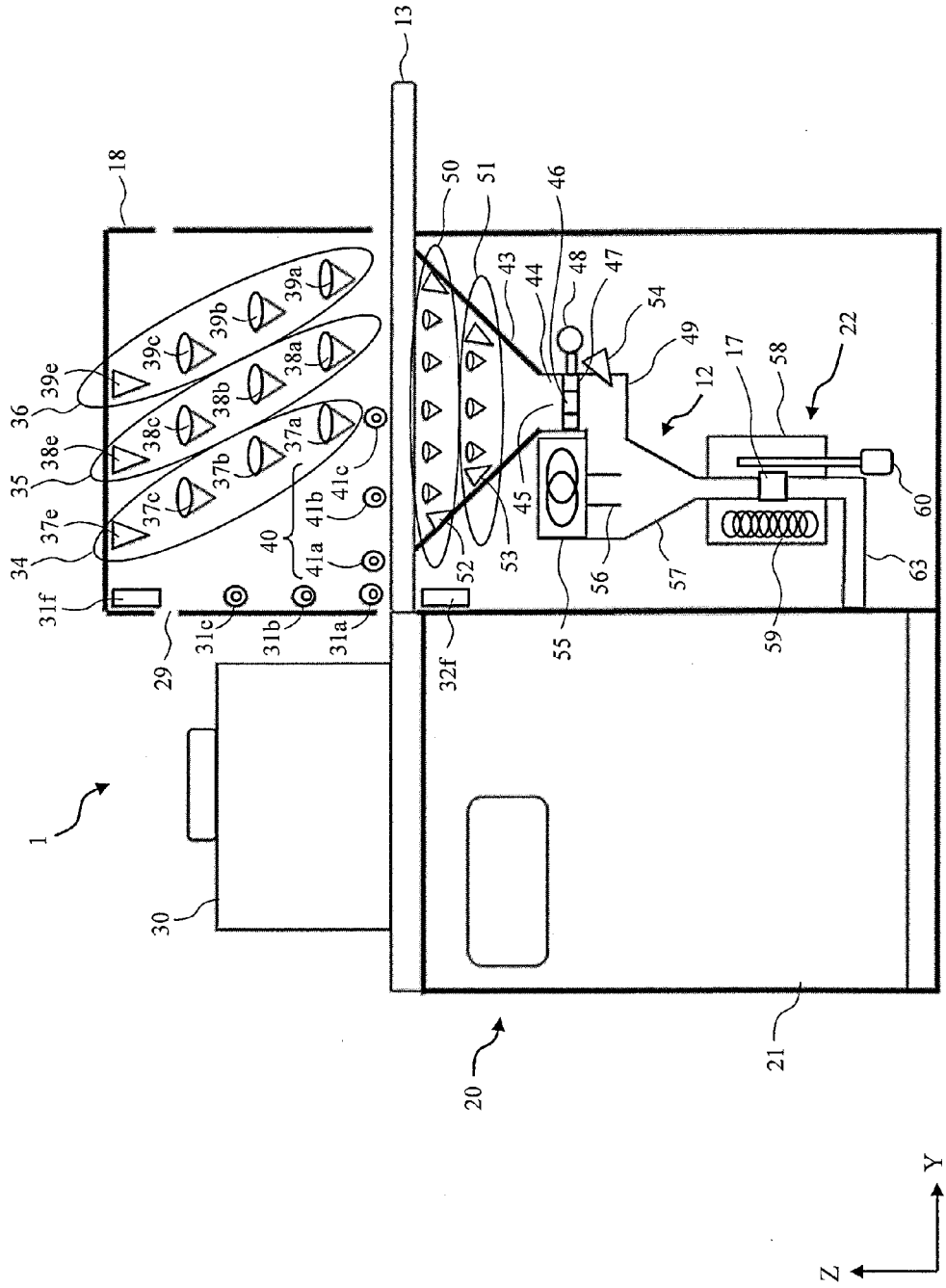

FIG. 7

|  | na,ni | nb,nh | nc, ng | nd | ne | nf |
|---|---|---|---|---|---|---|
| 32a,32f | 0.25 | 0.25 | / | / | 0.25 | / |
| 32a,32e,32f,32g | 0.15 | 0.15 | / | / | 0.25 | / |
| 32a,32d,32e,32f,32g,32h | 0.05 | 0.05 | / | 0.25 | 0.25 | 0.25 |
| 32a or 32b,32f | 0.25 | 0.25 | 0.25 | / | 0.15 | / |
| 32a or 32b,32e,32f,32g | 0.15 | 0.15 | / | / | 0.15 | / |
| 32a or 32b,32d,32e,32f,32g,32h | 0.05 | 0.05 | / | 0.15 | 0.15 | 0.15 |
| 32a or 32c,32f | 0.05 | 0.05 | 0.25 | / | 0.05 | / |
| 32a or 32c,32e,32f,32g | 0.15 | 0.15 | 0.15 | / | 0.05 | / |
| 32a or 32c,32d,32e,32f,32g,32h | 0.05 | 0.05 | 0.1 | 0.05 | 0.05 | 0.05 |

| | na | nb | nc | nd | ne | nf | ng | nh | ni |
|---|---|---|---|---|---|---|---|---|---|
| 32a,32d | 0.05 | 0.15 | / | 0.25 | / | / | / | / | / |
| 32a,32d,32e | 0.05 | 0.15 | / | 0.25 | / | / | / | / | / |
| 32a,32d,32e,32f | 0.05 | 0.25 | / | 0.25 | 0.25 | / | / | 0.25 | 0.2 |
| 32a,32d,32e,32f,32g | 0.05 | 0.25 | / | 0.25 | 0.25 | / | / | 0.25 | 0.15 |
| 32a,32d,32e,32f,32g,32h | 0.05 | 0.25 | / | 0.25 | 0.25 | 0.25 | / | 0.25 | 0.05 |
| 32a or 32b,32d | 0.05 | 0.05 | 0.15 | 0.15 | / | / | / | / | / |
| 32a or 32b,32d,32e | 0.05 | 0.05 | 0.2 | 0.15 | / | / | / | / | / |
| 32a or 32b,32d,32e,32f | 0.05 | 0.05 | 0.2 | 0.15 | 0.15 | / | / | 0.2 | 0.2 |
| 32a or 32b,32d,32e,32f,32g | 0.05 | 0.05 | 0.2 | 0.15 | 0.15 | / | / | 0.15 | 0.15 |
| 32a or 32b,32d,32e,32f,32g,32h | 0.05 | 0.05 | 0.2 | 0.15 | 0.15 | 0.15 | 0.25 | 0.1 | 0.05 |
| 32a or 32b or 32c,32d | 0.05 | 0.05 | 0.05 | 0.05 | / | / | / | / | / |
| 32a or 32b or 32c,32d,32e | 0.05 | 0.05 | 0.05 | 0.05 | / | / | / | / | / |
| 32a or 32b or 32c,32d,32e,32f | 0.05 | 0.05 | 0.05 | 0.05 | 0.05 | / | 0.2 | 0.2 | 0.2 |
| 32a or 32b or 32c,32d,32e,32f,32g | 0.05 | 0.05 | 0.05 | 0.05 | 0.05 | / | 0.15 | 0.15 | 0.15 |
| 32a or 32b or 32c, 32d,32e,32f,32g,32h | 0.05 | 0.05 | 0.05 | 0.05 | 0.05 | 0.05 | 0.1 | 0.05 | 0.05 |

FIG. 18

|     | na,ni | nb,nh | nc,ng | nd,nd,ne |
|-----|-------|-------|-------|----------|
| 32a | 0.05  | 0.05  |       | 0.25     |
| 32b | 0.05  | 0.05  |       | 0.15     |
| 32c | 0.05  | 0.05  | 0.1   | 0.05     |

FIG. 26

ATTACHED MATTER TESTING DEVICE AND TESTING METHOD

TECHNICAL FIELD

The present invention relates to a technique of detecting a substance (sample substance) attached to a detecting target, and mainly relates to a trace detecting system and a trace detecting method to detect a substance attached to baggage or a human body.

BACKGROUND ART

Patent Literatures 1 to 4 describe techniques of detecting the presence or not of dangerous substances such as explosives and narcotics in baggage at the boarding gate of airports, ports or the like. Patent Literature 5 describes a technique of changing the pressure of fluid in accordance with the shape and dimensions of a target object.

Patent Literature 1 describes a trace detecting system that moves a joint, thus moving a nozzle in accordance with the outer shape of a detecting target to blow compressed gas on the surface of the detecting target at the rate of the air velocity of 20 m/s or more. Patent Literature 2 describes a trace detecting system including a nozzle that blows compressed gas on the surface of a detecting target at the rate of the air velocity of 20 m/s or more, thus blowing the compressed gas to the inner wall of a collecting section as well as an arm holding the nozzle. Patent Literature 3 describes a technique of making an inspector wipe out the surface of baggage with a wiping member and determining the presence or not of a dangerous material and the type of it on sample microparticles attached to the wiping member. Patent Literature 4 describes a technique of including a sampling head that extends over the overall width of a sampling chamber to store baggage, the sampling head including a rotary brush to sweep the exposed face of the baggage and brings such a sampling head into contact with the surface of the baggage using a spring, a sensor or a servo, thus collecting sample microparticles attached to the surface of the baggage. Patent Literature 5 describes a spraying system to dynamically determine the fluid pressure (fan-air pressure, atomizing air pressure and the like) corresponding to a moving target object or a part of a moving target object, and capable of dynamically varying the liquid discharge pattern from a plurality of nozzles held at a common header.

CITATION LIST

Patent Literatures

Patent Literature 1: JP 2009-031316 A
Patent Literature 2: JP 2009-031315 A
Patent Literature 3: JP 2004-301749 A
Patent Literature 4: JP 9-126965 A (1997)
Patent Literature 5: JP 2008-544836 A

SUMMARY OF INVENTION

Technical Problem

The techniques described in Patent Literatures 1, 2 stop baggage in a sampling room once, and then calculate the virtual outer shape of the baggage based on a plurality of output signals that are obtained using pairs of transmitters and receivers disposed laterally and longitudinally at the entry of the sampling room to recognize the baggage and move the air nozzle attached at a forwarding end of the arm along the calculated virtual outer shape. After finishing scanning with the air nozzle by the arm, the baggage is conveyed from the sampling room to the outside. This technique has a problem of a longer duration to inspect one piece of baggage because the baggage has to be stopped once in the sampling room and then be scanned with the air nozzle. To scan with the air nozzle requires the arm having a joint and a moving mechanism to move the arm straight ahead, and so this technique has another problem of high probability of failure. There is still another problem of contamination of the device because the device has a lot of driving mechanisms and so easily generates dust therefrom.

The technique described in Patent Literature 3 requires the inspector to wipe off the entire face of the detection target with a wiping member. The part or the force to wipe off varies from one inspector to another, and this technique has a drawback of variations of the detection conditions. To wipe off the entire face of baggage, it takes time to inspect one detection target. This requires a plurality of inspectors to be positioned, leading to another problem of increase in detection cost. The rotary brush disclosed in Patent Literature 4 comes into contact with only the outermost surface of the baggage having complicated bumps and dips such as a handle and a zipper, and so the detection parts are limited unfortunately. The likelihood of accidents also may increase when the rotary brush is pushed against the surface of baggage, such as breakage of the surface of the baggage or breakage of items inside the baggage.

Patent Literature 5 relates to a spray gun for liquid-coating of a target, which is a technique of spraying liquid for coating while changing the application range of the liquid in the direction orthogonal to the moving direction of the target by dynamically changing the fan air pressure and the atomizing air pressure supplied to the spray gun, and is not for removing microparticles from the surface of baggage or the like.

It is an object of the present invention to provide a trace detecting system capable of removing sample microparticles from the surface of baggage in a non-contact manner without requesting the inspector's skill, and inspecting whether the sample microparticles contain a dangerous substance or not.

Solution to Problem

A trace detecting system of the present invention includes: a removal section including a plurality of air nozzles fixed to an inner wall thereof to spray air jet from the air nozzles to an inspection target that is conveyed inside thereof and remove a sample substance attached to the inspection target; a detection section to detect the removed sample substance; conveyance means to convey the inspection target; a size detection section to detect a size of the inspection target that is conveyed by the conveyance means; and an air nozzle control section to control operations of the plurality of air nozzles. The air nozzle control section selects an air nozzle capable of spraying air jet at 15 m/s or more to the surface of the inspection target based on an output signal from the size detection section, and makes the selected air nozzle spray air jet.

Such a configuration can remove a sample substance attached to the inspection target by air pressure of the air jet, thus increasing the amount of the sample substance to be detected at the detection section, while reducing variations in detection conditions.

Preferably, the trace detecting system further includes: a separator section to separate sample microparticles from air including the sample substance; and a conical shaped collector section to guide air including a sample substance from the removal section to the separator section. The collector section includes a plurality of air nozzles at an inner face thereof to blow air jet. In one example, the separation section utilizes a cyclone phenomenon, and a L-shaped pipe jointing the collector section and the separation section includes a nozzle at an inner face thereof to blow air jet.

This configuration can detect a sample substance such as sample microparticles attached to the inner face of the collector section and the inner face of the L-shaped pipe, and so the detection sensitivity can be improved. This also can prevent erroneous detections caused by a sample substance attached to the inner face of the collector section and the inner face of the L-shaped pipe that is removed during the inspection of the next inspection target.

The trace detecting system further may be equipped with a self-cleaning function to spay air jet to the inner wall of the removal/collection section, and so the trace detecting system can discharge a sample substance, dust and the like remaining inside of the removal/collection section. This can reduce the impurity at the inspection of the next inspection target, and so the detection can be performed reliably.

The trace detecting system further may include means to replace a collection filter of the separator section automatically, and so the detection can be performed always using a clean collection filter without stopping the system. As a result, the detection can be performed reliably.

Advantageous Effects of Invention

According to the present invention, sample microparticles attached to an inspection target can be removed and collected from the moving inspection target without touching the inspection target, and the amount of the sample microparticles collected can be increased. As a result, the sample substance can be identified easily and precisely.

Problems, configurations, and advantageous effects other than those described above will be made clear by the following description of embodiments.

BRIEF DESCRIPTION OF DRAWINGS

FIG. 4 is a side view explaining an exemplary configuration of the trace detecting system.

FIG. 7 shows an exemplary relationship between signals of a baggage detector and air nozzles to be used.

FIG. 8 is a timing chart showing spraying timings of air nozzles.

FIG. 17 shows another exemplary relationship between signals of a baggage detector and air nozzles to be used.

FIG. 18 shows still another exemplary relationship between signals of a baggage detector and air nozzles to be used.

FIG. 26 is a timing chart showing spraying timings of air nozzles.

DESCRIPTION OF EMBODIMENTS

The following describes embodiments of the present invention in details, with reference to the drawings. The following description deals with, as a typical detecting target, belongings of a subject, to which explosive microparticles or microparticles of explosive additives may be attached, and other possible detecting targets may include explosive substances, drugs such as a stimulant, chemical substances adversely affecting humans, microorganisms such as bacteria and viruses adversely affecting humans as well as mail, a human body and products exported and imported, to which a dangerous substance containing a substance that is typically expected to adversely affect humans is attached.

EXAMPLE 1

Figure 1:
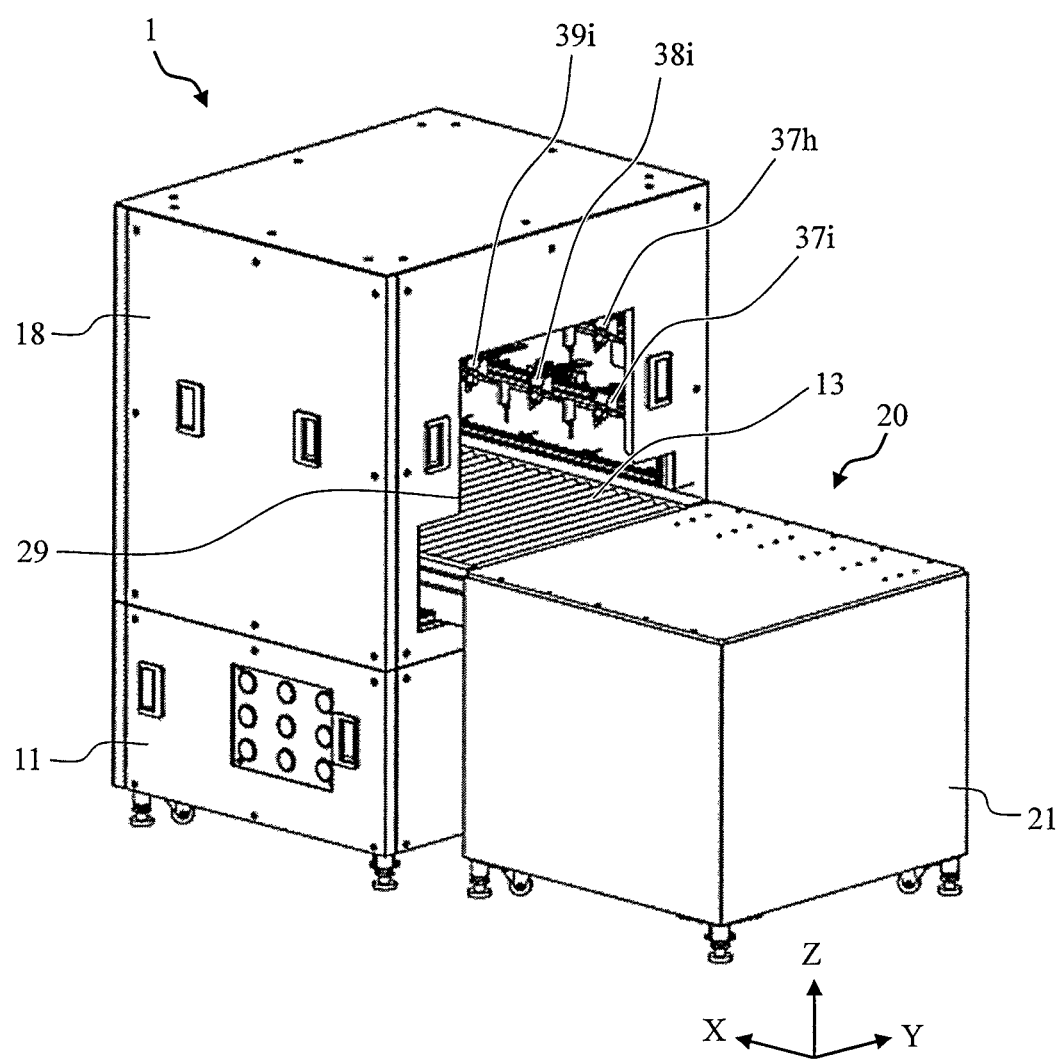
FIG. 1 is a perspective view showing an embodiment of the trace detecting system according to the present invention.
Figure 2:
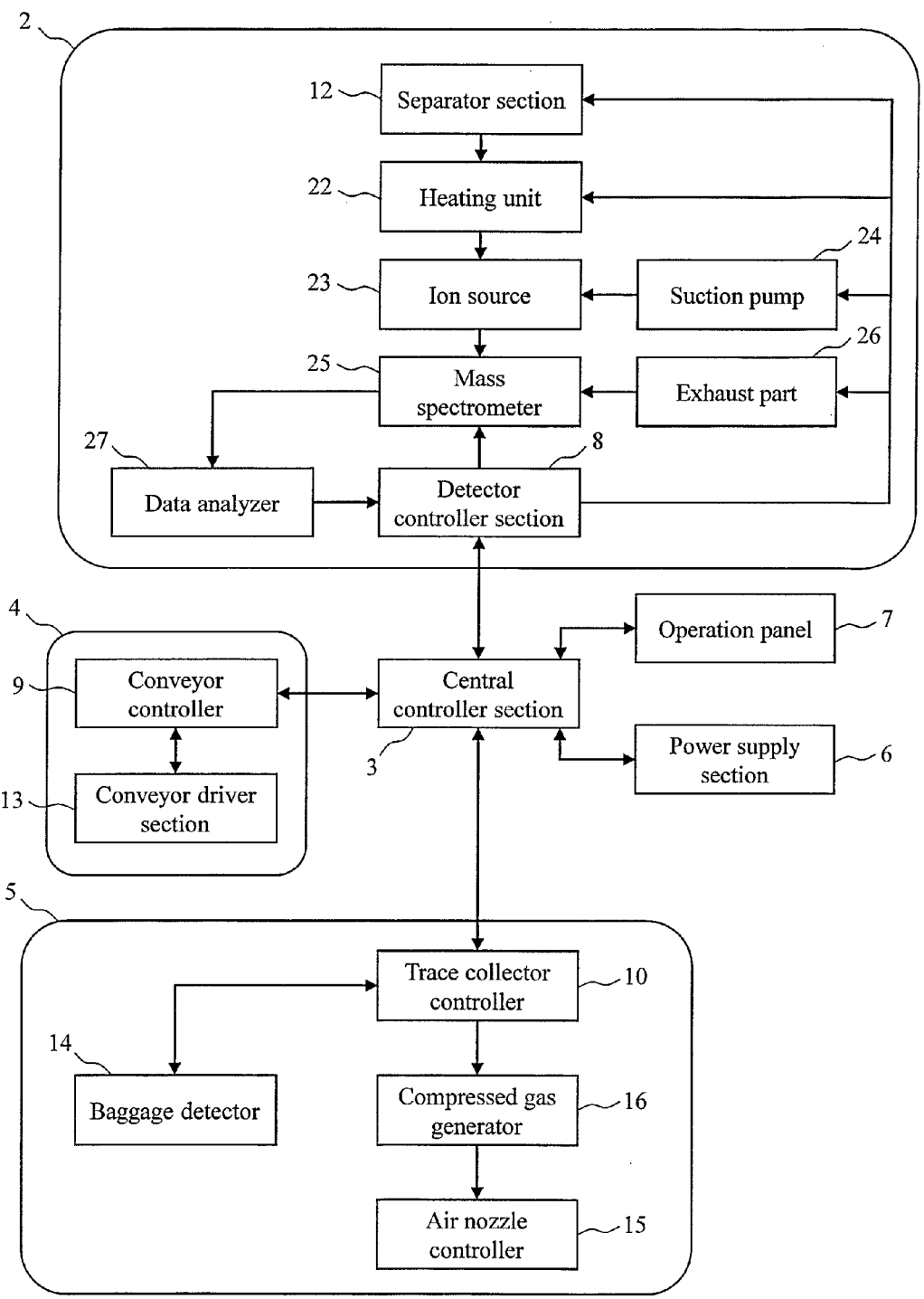
FIG. 2 is a block diagram showing an exemplary configuration of a major part of the trace detecting system.

FIG. 1 is a perspective view showing the appearance of an exemplary trace detecting system according to the present invention, and FIG. 2 is a block diagram showing its major configuration.

As shown in FIG. 2, this trace detecting system 1 includes a trace detecting section 2, a central controller section 3, a baggage conveyor section 4, a trace collector section 5, a power supply section 6 and an operation panel 7. The power supply section 6 to supply power required for the operations of various sections of the system is controlled by the central controller section 3. The central controller section 3 is connected to a detector controller section 8, a conveyor controller 9 and a trace collector controller 10. Operation conditions of the various sections of the system are input from the operation panel 7, and the central controller section 3 controls the operation of various sections of the system in accordance with the input operation conditions.

The trace detecting system unit 11 shown in FIG. 1 is internally provided with a separator section 12 and a heating unit 22 of the trace detecting section 2, the baggage conveyor section 4 and the trace collector section 5 shown in FIG. 2. A preparation table 20 has a mainframe 21 that is internally provided with the trace detecting section 2 other than the separator section 12 and the heating unit 22, the power supply section 6 and the central controller section 3 shown in FIG. 2. Baggage as a detecting target is conveyed by the baggage conveyor section 4 while being loaded on a netlike conveying tray (not illustrated). The size of the baggage is determined by a baggage detector 14 during conveyance, and the trace collector controller 10 determines a nozzle to be used and a spraying condition of air jet such as pressure of compressed air that are suitable for the determined size. The determined spray condition is transmitted to an air nozzle controller 15, and the air nozzle controller 15 adjusts pressure of compressed air supplied from a compressed gas generator 16 and controls driving of the nozzle to be used. The pressure is adjusted by an electropneumatic regulator (not illustrated) disposed at the air nozzle controller 15. To remove sample microparticles from the baggage, air jet is applied downward sequentially from above the baggage to the surface of the baggage.

The separator section 12 is disposed below a conveyor driver section 13, the separator section 12 being provided with a collection filter to collect sample microparticles removed from the baggage. The trace detecting system unit 11 has a sampling room 18 having an inner face covered with a cover (not illustrated). The operation panel 7 (not illustrated) is placed at a desired position for easy operation.

The collection filter 17 (see FIG. 3A) to collect sample microparticles is kept at a constant temperature by the heating unit 22. The heating unit 22 is connected to an ion source 23. Sample microparticles collected at the collection filter 17 are heated by the heating unit 22. The heated sample microparticles are vaporized, thus generating sample gas. The sample gas is introduced into the ion source 23 by a suction pump 24, and is ionized. Ions generated at the ion source 23 are subjected to mass spectrometry by a mass spectrometer 25. Air of the ion source 23 and the mass spectrometer 25 is exhausted by an exhaust part 26. A data analyzer 27 has storage means to store a database containing reference mass spectrometry data (the value of mass-to-charge ratio (mass number of ions/valence of ions) and relative intensity) that is required to identify a plurality of explosive substances. The mass spectrometer 25 includes a mass spectrometer having a detector, and an output signal from the detector is sent to the data analyzer 27, where data processing is performed, such as matching between database read from the storage means and a result of mass spectrometry of ions resulting from explosive components, thus identifying explosive substances. The identified explosive substances and/or the result of mass spectrometry are displayed at the operation panel 7.

Referring to FIGS. 3A, 3B, 4 and 5, the following describes the configuration of the baggage detector 14 of the trace collector section 5 and air nozzles of the trace detecting system 1 of the present embodiment.

Figure 3A:
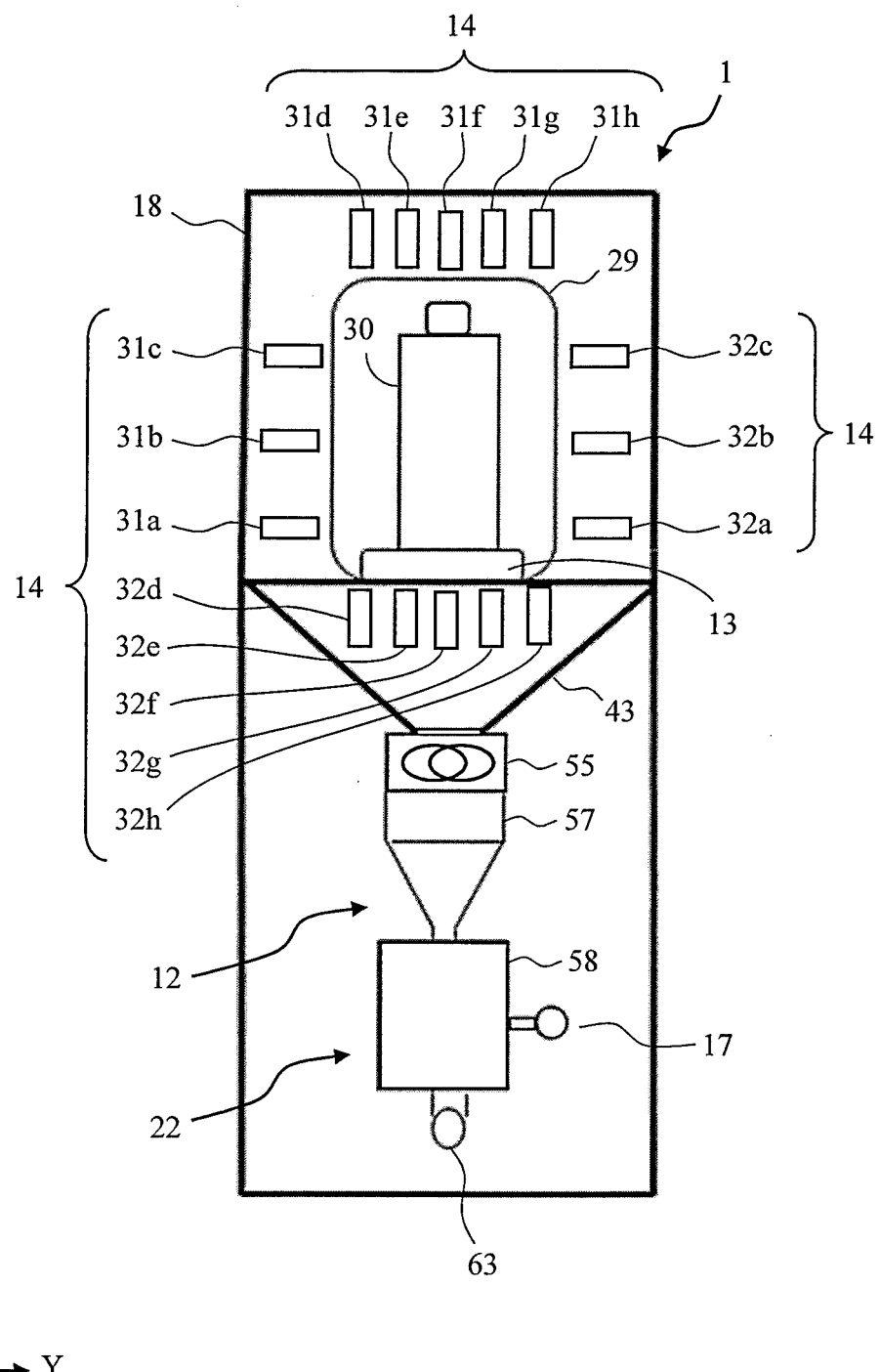
FIG. 3A explains an exemplary configuration of a baggage detector of the trace detecting system.
Figure 3B:
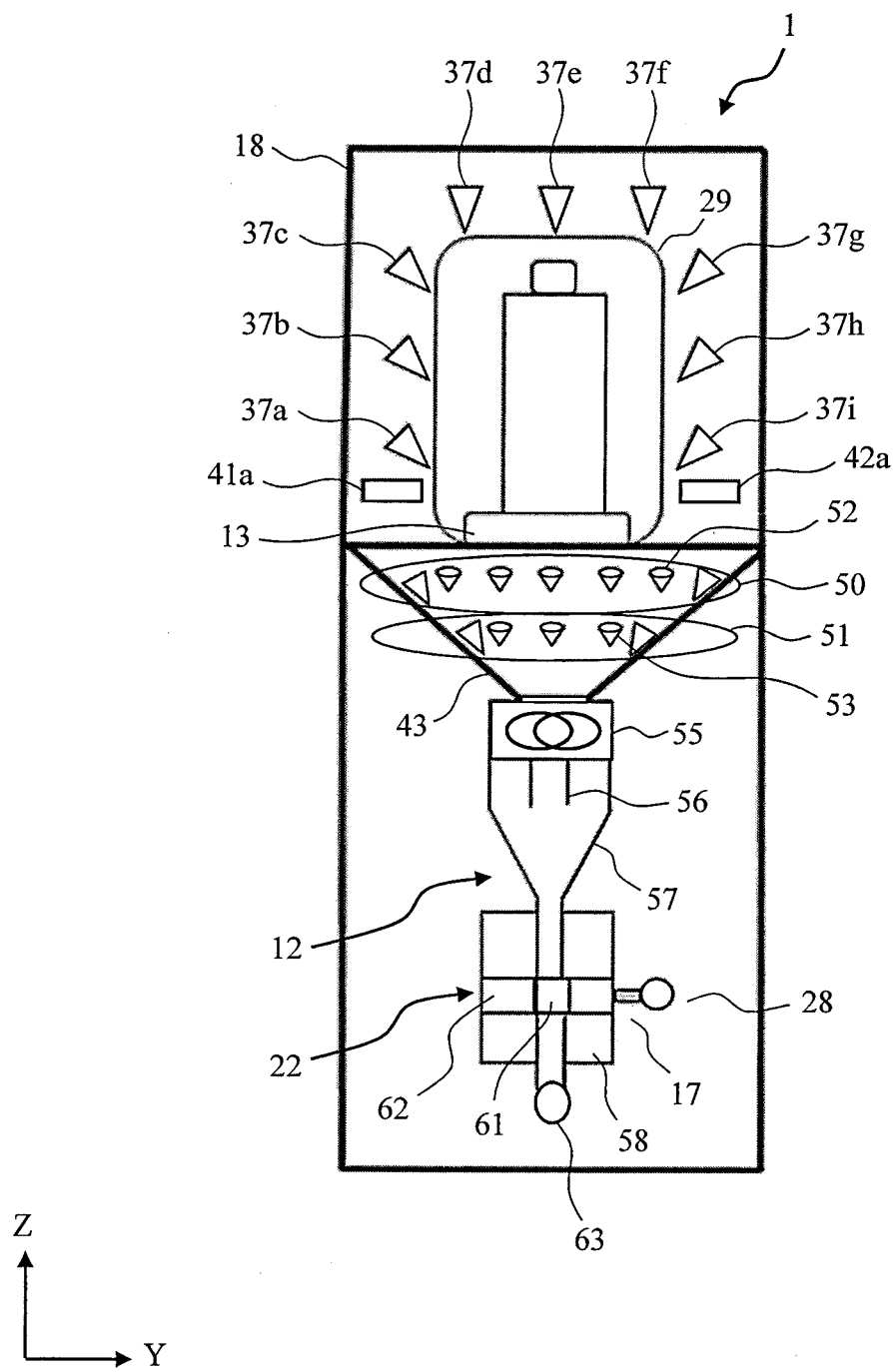
FIG. 3B explains an exemplary configuration of air nozzles of the trace detecting system.

FIGS. 3A and 3B are front views describing the configuration of the baggage detector 14 of the trace collector section 5 and air nozzles of the trace detecting system 1 of the present embodiment. The front views in FIGS. 3A and 3B are viewed from the negative direction of X-axis. FIG. 3A describes the baggage detector 14, and omits the illustration of parts other than the baggage detector 14, the separator section 12 and the heating unit 22. FIG. 3B describes the configuration of air nozzles, and omits the illustration of parts other than air nozzle groups, the separator section 12 and the heating unit 22.

FIG. 4 is a side view including a partial cross-section of the trace detecting system 1 to describe the configuration of the baggage detector 14 and air nozzle groups 34, 35 and 36 as well as the separator section 12 and the heating unit 22. The cross-section of FIG. 4 is a section that passes through the center of the sampling room 18 and is parallel to the baggage conveyance direction of the sampling room 18. The side view is viewed from the positive direction of Y-axis, and omits the illustration of parts other than the baggage detector 14 and the air nozzle groups 34, 35 and 36 as well as the separator section 12, the heating unit 22 and the preparation table 20.

Figure 5:
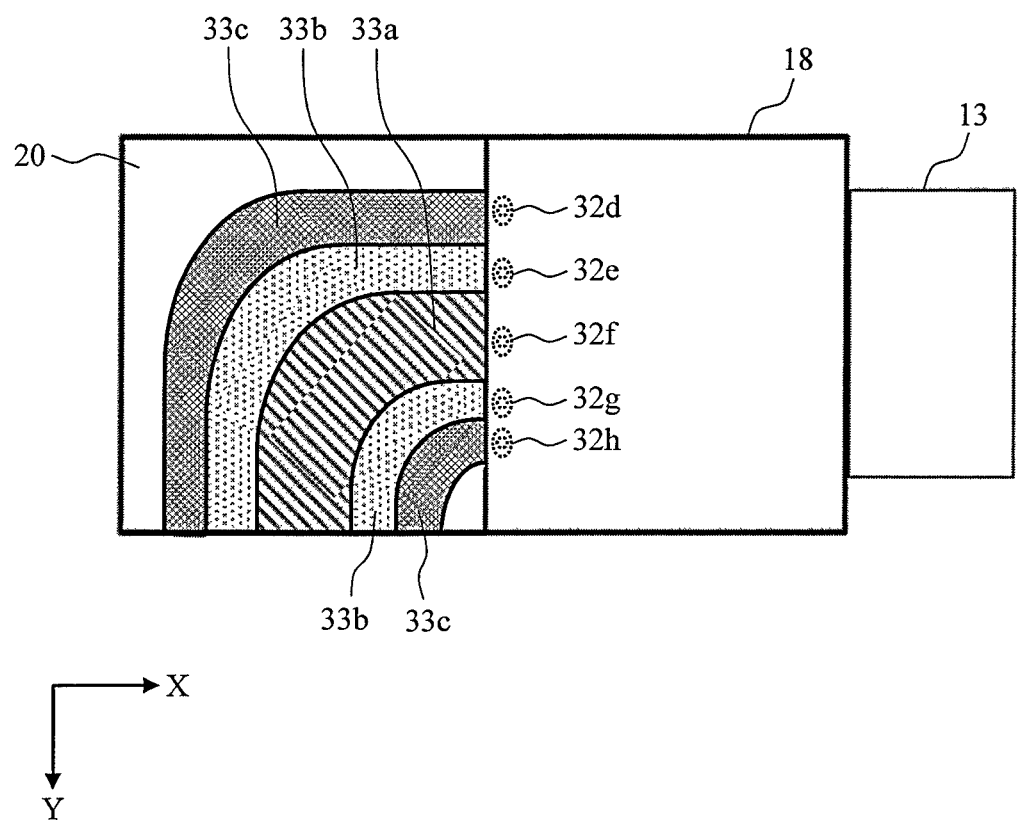
FIG. 5 shows exemplary lanes to guide baggage to a sampling room.

FIG. 5 is a top view showing the appearance of the trace detecting system 1, which is viewed from the positive direction of Z-axis. Baggage as a detecting target is conveyed into the sampling room 18 by the conveyor driver section 13 while being loaded on a netlike conveying tray (not illustrated). The sampling room 18 of the present embodiment has a sampling room entry 29 to allow for the passage of baggage that measures 60 cm in width and 50 cm in height.

As shown in FIG. 3A, the baggage detector 14 is disposed at the sampling room entry 29. This baggage detector 14 includes transmitters 31a to 31c to apply light and receivers 32a to 32c to receive light from the transmitters 31a to 31c that are disposed laterally across the conveyance path of baggage 30 and are opposed to each other, and includes transmitters 31d to 31h and receivers 32d to 32h that are disposed vertically across the conveyance path of the baggage 30 and are opposed to each other. The receivers 32a to 32h are configured to output signals when the baggage 30 blocks light from the transmitters 31a to 31h and so the receivers 32a to 32h do not receive light, and signals from the receivers 32a to 32h are transmitted to the air nozzle controller 15 via the trace collector controller 10.

The baggage detector 14 of the present embodiment includes the three pairs in total of transmitters 31a to 31c and receivers 32a to 32c that are disposed laterally at positions of 8 cm, 24 cm and 40 cm, respectively, in height from the conveyance face of the conveyor driver section 13, and includes the five pairs in total of transmitters 31d to 31h and receivers 32d to 32h that are disposed vertically at positions of the center of the sampling room entry 29, positions away from the center to left and right by 7.5 cm and positions away from the center to left and right by 15cm.

At airports, the maximum size of the baggage 30 that is allowed to carry onto the plane is specified as 110 cm or less that is the total of three sides of the baggage, for example. There are various types of the baggage 30 including small items such as wallets, handbags and trolley bags.

As shown in FIG. 5, the present embodiment provides three-different color painted lanes 33a to 33c at the surface of the preparation table 20 that is located upstream of the conveyor driver section 13 so as to remove sample microparticles effectively from the surface of various sized baggage. The blue lane 33*a* shows the range, through which small items are to be inserted into the sampling room 18, and specifically this is used as a mark to guide the baggage 30 to a part between the receivers 32*e* to 32*g* at the center of the sampling room 18 shown in FIG. 3A. The green lane 33*b* shows the range, through which relatively medium-sized baggage 30 such as handbags is to be inserted into the sampling room 18, and specifically this is to guide the baggage 30 to a part between the midst of the receivers 32*d* and 32*e* and the midst of the receivers 32*g* and 32*h* at the center of the sampling room 18 shown in FIG. 3. The red lane 33*c* shows the range, through which large-sized baggage 30 such as trolley bags is to be inserted into the sampling room 18, and specifically this is to guide the baggage 30 to the range that the receivers 32*d* and 32*h* at the center of the sampling room 18 shown in FIG. 3 detect. The lanes 33*a* to 33*c* of the present embodiment have color painted thereon to be an arc shape about the standing position of the inspector toward the outside of the opening of the sampling room 18 so as to be suitable to the motion of the inspector who moves the baggage 30 to the sampling room 18. The inspector decides the introduction position of the baggage 30 into the sampling room 18 depending on the size of the baggage 30 using the lanes 33*a* to 33*c* as criterion, thereby enabling effective removal of sample microparticles from the surface of the baggage and so stable inspection.

As shown in FIGS. 3B and 4, the air nozzle groups 34, 35, 36 are disposed in the sampling room 18 to blow air jet to both side faces and a top face of the baggage 30. The following describes one air nozzle group 34 as an example. It includes three air nozzles 37*a*, 37*b*, 37*c* (and air nozzles 37*g*, 37*h* and 37*i*) at the side faces of the sampling room entry 29 at intervals of 16 cm from the height of the conveyance face, and three air nozzles 37*d*, 37*e*, 37*f* (the drawing shows the air nozzle 37*e* only) on the upper side of the sampling room 18 at the center of the sampling room entry 29 and intervals of 15 cm to left and right from the center. The first air nozzle group 34 includes the combination of these nine air nozzles in total of the air nozzles 37*a* to 37*i*, and other air nozzle groups 35 and 36 having a similar nozzle configuration are disposed in the depth direction of the sampling room 18.

Referring to the side view of FIG. 4, the following describes the air nozzle groups 34, 35 and 36 that are disposed in the depth direction of the sampling room 18.

The air nozzle group that is the closest to the sampling room entry 29 is referred to as the first air nozzle group 34, the air nozzle group at the center of the sampling room 18 is referred to as the second air nozzle group 35, and the air nozzle group that is the closest to the exit of the sampling room 18 is referred to as the third air nozzle group 36.

To begin with, the following describes the first air nozzle group 34. The other second air nozzle group 35 and third air nozzle group 36 also have the same configuration as that of the first air nozzle group 34.

The first air nozzle group 34 includes the air nozzles 37*d*, 37*e* and 37*f* to blow air jet to the top face of the baggage 30, which are disposed at an upper part of the sampling room 18 and at a position of 55 cm in height from the height of the conveyance face. FIG. 4 shows the air nozzle 37*e* at the center only. The first air nozzle group 34 includes the air nozzles 37*a*, 37*b*, 37*c*, 37*g*, 37*h* and 37*i* to blow air jet to the side faces of the baggage 30, which are disposed at positions from the center of the sampling room 18 to left and right by 35 cm. As shown in FIG. 3B, the air nozzles 37*g*, 37*h* and 37*i* are disposed on the inner wall on the opposite side of the sampling room 18, and so they are not illustrated in FIG. 4. The air nozzles 37*c* and 37*g* are shifted from the air nozzles 37*d*, 37*e* and 37*f* by 5 cm in the depth direction of the sampling room 18. The air nozzles 37*b* and 37*h* are shifted from the air nozzles 37*c* and 37*g* by 5 cm in the depth direction of the sampling room 18. Similarly, the air nozzles 37*a* and 37*i* are shifted from the air nozzles 37*b* and 37*h* by 5 cm in the depth direction of the sampling room 18. The air nozzle group including this combination makes up the first air nozzle group 34.

The second air nozzle group 35 includes the air nozzles 38*d*, 38*e* and 38*f*, which are disposed at an upper part of the sampling room 18 and at a position away from the air nozzles 37*d*, 37*e* and 37*f* by 5 cm. The other air nozzles 38*a*, 38*b*, 38*c*, 38*g*, 38*h* and 38*i* of the second air nozzle group 35 have the same positional relationship as the air nozzles 37*a*, 37*b*, 37*c*, 37*g*, 37*h* and 37*i* of the first air nozzle group 34 and are disposed on the inner walls of the sampling room 18.

Similarly, the third air nozzle group 36 includes the air nozzles 39*d*, 39*e* and 39*f*, which are disposed at an upper part of the sampling room 18 and at a position away from the air nozzles 38*d*, 38*e* and 38*f* by 5 cm. The other air nozzles 39*a*, 39*b*, 39*c*, 39*g*, 39*h* and 39*i* of the third air nozzle group 36 have the same positional relationship as the air nozzles 38*a*, 38*b*, 38*c*, 38*g*, 38*h* and 38*i* of the second air nozzle group 35 and are disposed on the inner walls of the sampling room 18.

As shown in FIG. 4, the sampling room 18 includes a trigger sensor 40 disposed, which detects timings of spraying of air jet from the aforementioned air nozzle groups 34, 35 and 36. The trigger sensor 40 includes transmitters and receivers, which are transmitters 41*a* to 41*c* to apply light and receivers 42*a* to 42*c* to receive light from the transmitters 41*a* to 41*c* that are disposed to be opposed to each other across the conveyance path of the baggage 30. FIG. 3B shows the relationship between the transmitter 41*a* and the receiver 42*a*. The receivers 42*a* to 42*c* of the trigger sensor 40 are configured to output signals when the baggage 30 blocks light from the transmitters 41*a* to 41*c* and the receivers 42*a* to 42*c* do not receive the light. Signals from the receivers 42*a* to 42*c* are transmitted to the air nozzle controller 15 via the trace collector controller 10.

A trigger sensor 40*a*, which is to detect timings to spray air jet from the air nozzles 37*d*, 37*e* and 37*f* of the first air nozzle group 34 disposed at an upper part of the sampling room 18, is disposed at a position away from the air nozzles 37*d*, 37*e* and 37*f* by 5 cm toward the side of the sampling room entry 29. A trigger sensor 40*b*, which is to detect timings to spray air jet from the air nozzles 38*d*, 38*e* and 38*f* of the second air nozzle group 35 disposed at an upper part of the sampling room 18, is disposed at a position away from the air nozzles 38*d*, 38*e* and 38*f* by 5 cm toward the side of the sampling room entry 29. Similarly, a trigger sensor 40*c*, which is to detect timings to spray air jet from the air nozzles 39*d*, 39*e* and 39*f* of the third air nozzle group 36 disposed at an upper part of the sampling room 18, is disposed at a position away from the air nozzles 39*d*, 39*e* and 39*f* by 5 cm toward the side of the sampling room entry 29.

Next, the following describes a trace collector 43, with reference to FIGS. 3A, 3B and 4. The trace collector 43 is disposed below the conveyor driver section 13, which is to collect sample microparticles removed from the surface of the baggage 30 and guide them to the separator section 12.

The trace collector 43 has an opening at the upper part having a rectangular shape and measuring 50 cm in width and 60 cm in depth, and a lower part of the trace collector 43 is connected to an air inlet pipe 44 having a circular cylindrical shape of 3.5 cm in inner diameter. The trace collector 43 has a conical shape of 41.5 cm in height. To the air inlet pipe 44, a coarse filter 45 that is of a drawer type facilitating insertion and pull-out is connected. The coarse filter 45 includes a stainless-steel coarse filter 46, a tray 47 to hold the stainless-steel coarse filter 46, and a handle 48 to be used for insertion and removal of the coarse filter to/from the air inlet pipe. The stainless-steel coarse filter 46 of the present embodiment has coarseness with an opening of 0.2 mm. The coarse filter 45 is connected to an L-shaped pipe 49 on the lower side, and the L-shaped pipe 49 is connected to an outer cylinder 57 of the separator section 12.

The trace collector 43 has an inner face, at which an upper air nozzle group 50 is disposed at a position of 2 cm from the upper opening and a lower air nozzle group 51 is disposed at a position of 17.5 cm from the upper opening for each face. The upper air nozzle group 50 is made up of five upper air nozzles 52 in total for each face, one of which is disposed at the center of the trace collector 43 and four of which are disposed to left and right of the center at intervals of 10 cm. The lower air nozzle group 51 is made up of three air nozzles 53 in total for each face, one of which is disposed at the center of the trace collector 43 and two of which are disposed to left and right of the center at intervals of 10 cm. The upper air nozzle group 50 and the lower air nozzle group 51 are to blow air jet to the inner face of the trace collector 43 so as to remove explosive microparticles attached to the inner face of the trace collector 43 and expel them to the exit side of the trace collector 43.

At the inner face of the trace collector 43, a sheet (not illustrated) made of tetrafluoroethylene that becomes negatively charged is applied so as to prevent adsorption of explosive microparticles that become negatively charged due to static electricity. The L-shaped pipe 49 has an inner face, at which an assist air nozzle 54 is disposed for sending assist air to blow air jet to the outer cylinder of the separator section 12.

Next, the following describes the separator section 12 of the present embodiment, with reference to FIGS. 3A, 3B and 4.

The separator section 12 of the present embodiment utilizes a cyclone phenomenon. The separator section 12 includes an exhauster 55, an inner cylinder 56 connected to the exhauster 55 and an outer cylinder 57 having a circular cone shape. The exhauster 55 exhausts air inside of the outer cylinder 57 via the inner cylinder 56. The outer cylinder 57 is connected to the L-shaped pipe 49 so as to be inscribed in the circumference of the outer cylinder 57. The outer cylinder 57 is connected to the heating unit 22 on its small-diameter side. The heating unit 22 is provided with a heating block 58, into which the collection filter 17 is inserted, a heater 59 to heat the heating block 58 to a certain temperature and keep the temperature, and a thermometer 60 to measure the temperature. The collection filter 17 to collect sample microparticles is inserted into the heating block 58. The collection filter 17 is of a cartridge type provided with a handle 28 so as to facilitate insertion and pulling-out of the filter to/from the heating block 58.

The thermometer 60 and the heater 59 of the heating block 58 are connected to the detector controller section 8, and can heat the temperature of the heating block 58 at any temperature from a room temperature to 300° C. and keep the temperature.

Next, an air nozzle to be used depending on the size of the baggage 30 and the pressure of air jet sprayed thereto are described below, with reference to FIGS. 6, 7 and 8.

The present inventors found from experiments that, to effectively remove explosive microparticles attached to baggage, it is effective to blow air jet at the air velocity of about 15 m/s or more to the surface of baggage intermittently from an upper position to a lower position of the baggage sequentially, and to effectively collect the removed explosive microparticles, it is important to suck air in the sampling room 18 while applying air jet.

Figure 6:
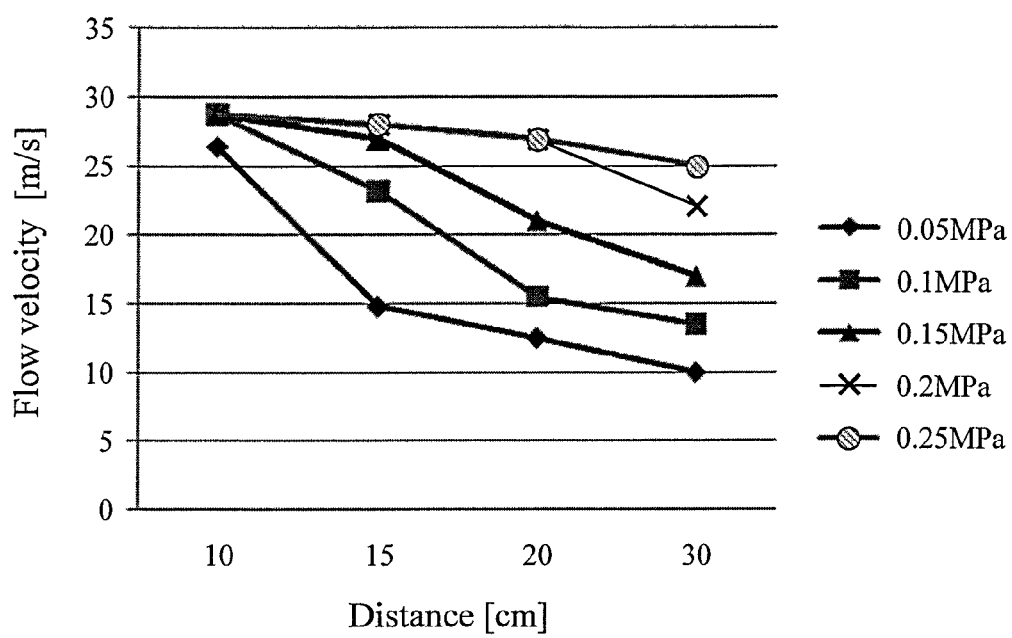
FIG. 6 is a graph showing relationships between the spraying distance of air jet sprayed from air nozzles and the air velocity thereof.

FIG. 6 shows results of measurement of a relationship between the distance from a nozzle tip end and the air velocity when pressure of air jet from an air nozzle of 1 mm in nozzle diameter was increased from 0.05 MPa to 0.25 MPa gradually by 0.05 MPa. The value of air velocity at the distance of 10 cm focused to about 28 m/s/for all values of pressure, because the air velocity exceeded the upper limit of measurement of the instrument used. It is found from this result that, in the case of the minimum pressure of 0.05 MPa, the air velocity at about 15 m/s or more can be obtained at the distance of about 15 cm or less. In the case of the maximum pressure of 0.25 MPa, although the velocity exceeded the measurement range, it is found by extrapolation that the distance of about 36 cm or less enables the air velocity at about 15 m/s or more.

Based on this result, the following describes an air nozzle to be used depending on the size of the baggage and the pressure of air jet applied thereto with reference to FIG. 7.

FIG. 7 shows the relationships among output conditions (output patterns) of signals from the receivers 32a to 32h of the baggage detector 14, the air nozzles to be used and pressure of air jet sprayed from the air nozzles. In FIG. 7, the receivers of the baggage detector 14 that are listed on the left column indicate that the corresponding receivers are outputting signals. For instance, "32a, 32f" in the second row of FIG. 7 indicates that the size of the baggage is small, and so only the lowest receiver 32a among the three receivers 32a to 32c disposed to detect a height does not receive light due to blocking by the baggage, and only the center receiver 32f among the five receivers 32d to 32h disposed to detect a width of the baggage does not receive light due to blocking by the baggage. In letters listed on the upper column of FIG. 7, i.e., na, nb, nc, nd, ne, nf, ng, nh and ni, n denotes numeral 37, 38 or 39.

Oblique lines in the table of FIG. 7 indicate air nozzles that are not used in the corresponding conditions. Values of pressure for air jet listed in the table of FIG. 7 indicate the values of pressure that enable the application of air jet at the air velocity of about 20 m/s to the surface of the baggage 30 having an intermediate size between the maximum size and the minimum size that is found from the signal outputs of the baggage detector 14, and the unit of the values is MPa. Spraying conditions shown in the table of FIG. 7 are stored in the trace collector controller 10 in advance.

In the case of the smallest baggage 30, the baggage detector 14 of the present embodiment outputs signals of the receivers 32a and 32f only. As described above referring to FIG. 5, the surface of the preparation table 20 has differently color-painted lanes 33a to 33c, and so the inspector can insert the baggage 30 at a substantially constant position into the sampling room 18. Therefore, the baggage detector 14 that detects baggage 30 is less likely to change depending on the size of the baggage 30.

When smallest baggage 30 enters the sampling room 18, air nozzles to spray air jet used are nozzles na, nb, ne, nh and ni only of each air nozzle group, and the pressure of air jet sprayed at that time is 0.25 MPa. For largest baggage 30, all receivers 32a to 32i of the baggage detector 14 output signals. In the case of such large baggage 30, air jet is sprayed from all air nozzles. The pressure of air jet at that time is set at 0.1 MPa for nozzles nc and ng only and at 0.05 MPa for other nozzles.

Following the trigger sensor 40 outputting a signal, spraying of air jet from the air nozzle groups 34, 35 and 36 is performed toward the baggage 30 from an upper part to a lower part of the baggage 30 sequentially and on a time-series basis. The following describes specific spraying timings of air jet.

Figure 8:
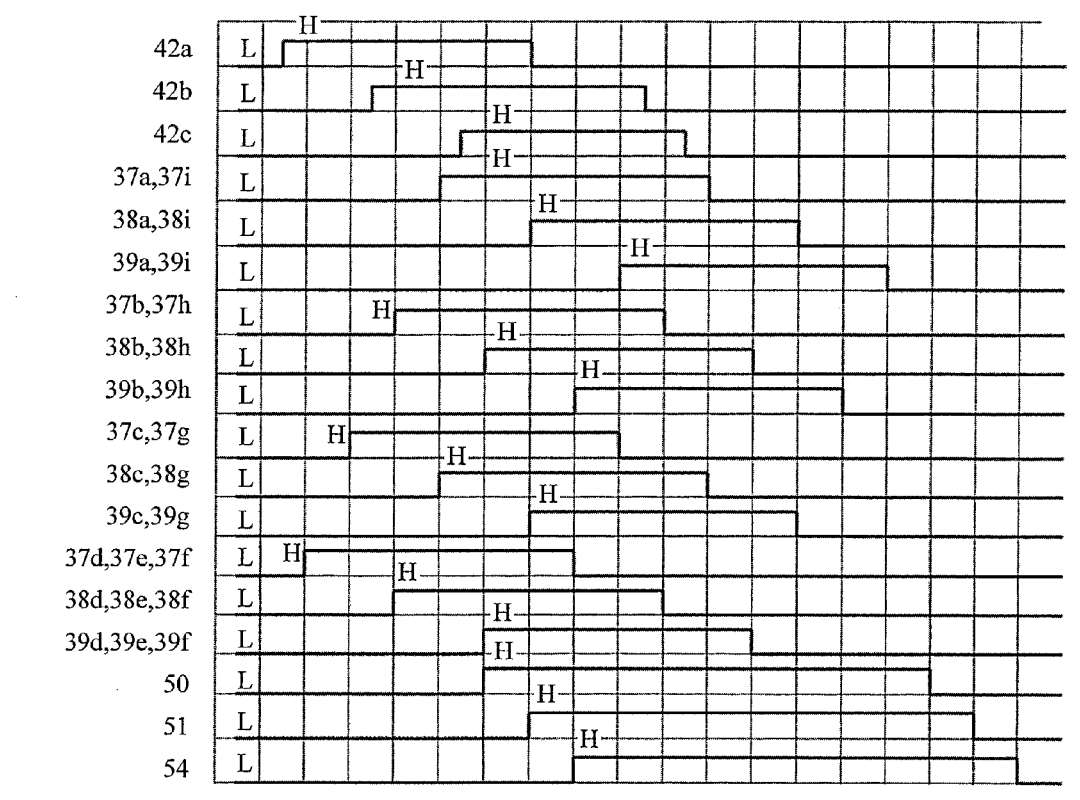

FIG. 8 is a time chart showing output signals of the receivers 42a to 42c of the trigger sensor 40 and operation timings of the air nozzles. The drawing shows states of the signals of the receivers 42a to 42c of the trigger sensor 40 and states of air-jet spraying of the air nozzles 37a to 37i, 38a to 38i, 39a to 39i, 52, 53 and 54 when the baggage 30 passes through the corresponding positions of the trigger sensor 40. The horizontal axis of FIG. 8 is a time axis, and the vertical axis thereof represents the states of the receiver 42 outputting signals as H and not outputting signals as L. Similarly, it represents the states of the air nozzles 37a to 37i, 38a to 38i, 39a to 39i, 52, 53 and 54 outputting signals as H and not outputting signals as L. In the present embodiment, the conveyance speed of the baggage 30 is set at 12 m/min.

The present inventors found from experiments that, in order to blow air jet to the baggage to effectively remove sample microparticles attached to the baggage, it is effective to blow the air jet to the baggage intermittently a plurality of times. Based on this finding, during duration H when air jet is sprayed in FIG. 8 of the present embodiment, the following spraying operation is repeated, i.e., air jet is sprayed for 0.1 sec., is stopped for 0.1 sec., and then is sprayed again for 0.1 sec. Such intermittent spraying of air jet enables removal of sample microparticles effectively from the baggage with a less consumption amount of compressed gas.

When the baggage 30 is conveyed into the sampling room 18 and the size of the baggage 30 is determined, then the trace collector controller 10 finds an air nozzle to be operated and pressure of compressed gas while referring to the table of FIG. 7, and transmits the same to the air nozzle controller 15. Then the air nozzle controller 15 sets spraying conditions shown in FIG. 7 at the air nozzles 37a to 37i, 38a to 38i and 39a to 39i. Conditions for the spraying pressure of air jet are set using a known electropneumatic regulator (not illustrated) disposed in the air nozzle controller 15. When the receiver 42a of the trigger sensor 40 outputs a signal, the air nozzles 37d, 37e and 37f of the first air nozzle group 34 start spraying, the air nozzles 37c and 37g start spraying 0.2 sec. later, the air nozzles 37b and 37h start spraying 0.2 sec. later, and the air nozzles 37a and 37i start spraying 0.2 sec. later. The reason why setting the intervals of starting spraying at 0.2 sec. is because it takes 0.25 sec. for the baggage to pass through a distance between the nozzles (5 cm), and so the sequence is set so that spraying is performed 0.05 sec. before the passage of the baggage.

When the air nozzles 37a and 37i of the first air nozzle group 34 spray air jet, the air nozzle 52 of the upper air nozzle group 50 of the trace collector 43 starts spraying 0.2 sec. later, and the air nozzle 53 of the lower air nozzle group 51 of the trace collector 43 starts spraying 0.2 sec., later. When the lower air nozzle group 51 of the trace collector 43 starts spraying of air jet, the assist air nozzle 54 provided at the L-shaped pipe 49 sprays air jet 0.2 sec. later. The pressure of the air jet of the upper air nozzle group 50 and the lower air nozzle group 51 of the trace collector 43 and the assist air nozzle 54 is fixed at 0.1 MPa.

Meanwhile, when the receiver 42b of the trigger sensor 40 outputs a signal, then the second air nozzle group 35 starts spraying in the same order as that of the first air nozzle group 34, and when the receiver 42c of the trigger sensor 40 outputs a signal, then the third air nozzle group 36 starts spraying in the same order as that of the first air nozzle group 34.

Air jet sprayed from the air nozzles 37d, 37e and 37f of the first air nozzle group 34 continues for 0.3 sec. after the signal output from the receiver 42a of the trigger sensor 40 becomes off. The duration of 0.3 sec. is set because, since the conveyance speed is set at 12 m/min. in the present embodiment and it takes 0.25 sec. for the baggage to pass through a distance of 5 cm between the receiver 42a of the trigger sensor 40 and the first air nozzle group 34, the duration is set at 0.3 sec. to be on the safe side. Similarly, when spraying of air jet from the air nozzles 37d, 37e and 37f ends, spraying of air jet from the air nozzles 37c and 37g ends 0.3 sec. later. Next, when spraying of air jet from the air nozzles 37c and 37g ends, spraying of air jet from the air nozzles 37b and 37h ends 0.3 sec. later. Next, when spraying of air jet from the air nozzles 37b and 37h ends, spraying of air jet from the air nozzles 37a and 37i ends 0.3 sec. later. The duration of 0.3 sec. is set because, since the conveyance speed is set at 12 m/min. in the present embodiment, and the distance between the air nozzles 37d, 37e and 37f and the air nozzles 37c, 37g, the distance between the air nozzles 37c and 37g and the air nozzles 37b and 37h, and the distance between the air nozzles 37b and 37h and the air nozzles 37a and 37i of the first air nozzle group 34 is 5 cm, and it takes 0.25 sec. for the baggage to pass through this distance, the duration is set at 0.3 sec. to be on the safe side.

When some air nozzles are not operated in FIG. 7, the air nozzles are held at the L state in FIG. 8. When one piece of baggage 30 has a size that is changed from a part thereof, such a change in size can be always detected by the baggage detector 14 at the sampling room entry 29. Therefore, even when the size of the baggage 30 changes during the conveyance of the baggage 30, the conditions listed in FIG. 7 can be applied to the air nozzle groups 34, 35, 36 before air jet is sprayed, and so the conditions to apply air jet to the baggage 30 can be always controlled to be the air velocity of about 15 m/s or more.

Figure 9:
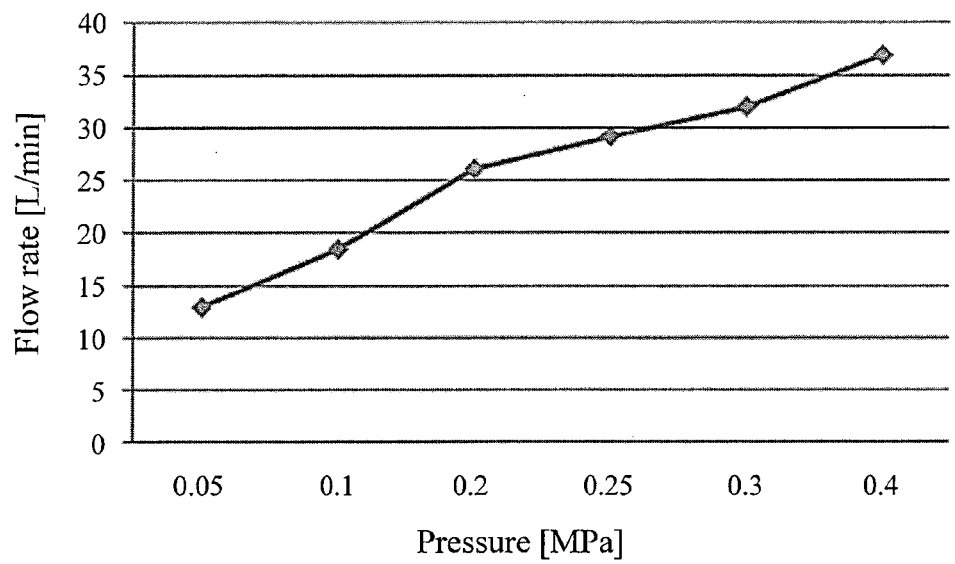
FIG. 9 is a graph showing a relationship between the consumed flow rate of air sprayed from an air nozzle and its pressure.

FIG. 9 shows a result of measurements about the pressure of air jet and the consumed flow rate when the air nozzle used has a diameter of 1 mm. The result of FIG. 9 shows that, when air jet is sprayed to largest baggage 30 under the conditions shown in FIG. 7, the consumed flow rate is 995 L/min. On the other hand, when spraying is performed from all of the nozzles with the maximum spraying pressure of 0.25 MPa, the consumed flow rate is 1,750 L/min. In this way, according to the present embodiment, sample microparticles can be removed from the baggage 30 with the consumed amount of air that is about ½ of the case of spraying from all of the nozzles with the maximum spraying pressure. As a result, the compressed gas generator used can be made compact.

According to the present embodiment, air jet can be blown to the baggage 30 under a constant condition enabling removal of sample microparticles from the baggage 30 from an upper part thereof sequentially, and so the removal can be performed effectively. Moreover, the flow rate of air jet consumed can be minimized.

Sample microparticles removed from the baggage 30 are sucked to the separator section 12 by the aforementioned exhauster 55 of the separator section 12 through the air inlet pipe 44 and the L-shaped pipe 49 connected to a lower part of the trace collector 43. At this time, dangerous substances, dust and the like removed from the baggage 30 also will be sucked with sucked air. Since the dust having a size larger than explosive substances is collected by the coarse filter 45, small substances only such as dangerous substances will be conveyed to the separator section 12 with air.

The present embodiment controls the air intake amount of the outer cylinder 57 by the exhauster 55 so that air flows at the rate of about 12 m/s at the connection port of the outer cylinder 57 and the L-shaped pipe 49 of the separator section 12, thus causing a cyclone phenomenon inside of the outer cylinder 57. Air sucked by the exhauster 55 containing dangerous substances forms a swirling flow going downward along the periphery of the inner face of the outer cylinder 57 having a circular cone shape. After such a swirling flow reaches a part around a lower part of the outer cylinder 57, it is sucked by the inner cylinder 56 and is discharged to the outside from the exhauster 55. At this time, sample microparticles settle out to a lower part of the outer cylinder 57 along the inner face of the outer cylinder 57, and are collected at the surface of the collection filter 17 in the heating unit 22 that is connected to the lower part of the outer cylinder 57.

The present inventors observed the particle size of actual explosives and found that the minimum size of the particles was 10 to 20 μm. Based on this finding, the collection filter 17 of the present embodiment used was a stainless steel filter 61 that has excellent heat resistance and such durability, is non-transparent and has coarseness with openings of 12.7 μm. Since the filter is a non-transparent filter, particles of 10 to 20 μm in size can be captured.

The collection filter 17 includes the stainless steel filter 61, a cartridge 62 to hold the stainless steel filter 61, and the handle 28 that is used to load the cartridge to the heating block 58. Since the collection filter 17 is inserted into the heating block 58 that is heated, the stainless steel filter 61 in the collection filter 17 also is heated to a temperature similar to that of the heating block 58. This means that sample microparticles attached to the stainless steel filter 61 are heated rapidly, and so vaporization of the sample microparticles is promoted rapidly, whereby sample gas is generated.

Figure 10:
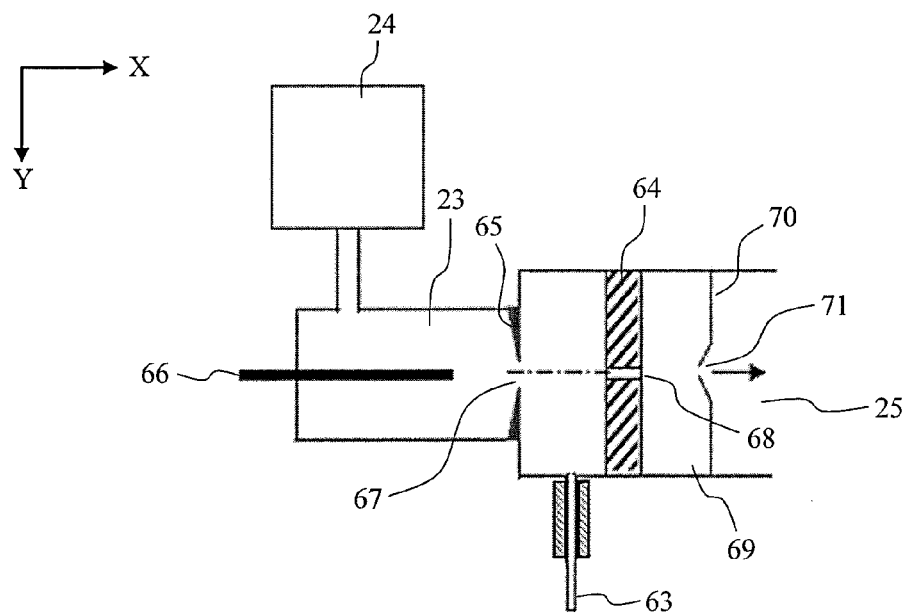
FIG. 10 describes an exemplary ion source of the trace detecting system.

Next, the following describes the trace detecting section 2 of the present embodiment, with reference to FIG. 10. FIG. 10 is a top view describing the configuration of the ion source 23 of the trace detecting section 2. FIG. 10 is viewed from the positive direction of Z-axis, and omits the illustration of parts of the trace detecting system 1 other than the ion source 23.

Sample gas generated in the heating block 58 is guided through an introducing pipe 63 by the suction pump 24 and is conveyed to a space between a first aperture electrode 64 and a counter electrode 65 of the ion source 23. The ion source 23 and the introducing pipe 63 are provided with a heater (not illustrated) and a thermometer (not illustrated). Supplying of electricity to this heater is controlled by the controller section in accordance with an output signal of the thermometer so as to always heat the ion source 23 and the introducing pipe 63 to a desired temperature and keep the temperature to prevent adsorption of the vaporized sample to the inside of the ion source 23.

The ion source 23 includes a needle electrode 66, and high voltage is applied between the needle electrode 66 and a counter electrode 65. Colon discharge occurs in the vicinity of the tip end of the needle electrode 66, and nitrogen, oxygen, water vapor and the like are firstly ionized. These are called primary ions. These primary ions are moved to the side of the counter electrode 65 by electric field. The vaporized sample that is conveyed to a space between the first aperture electrode 64 and the counter electrode 65 flows to a space where the needle electrode 66 is disposed via an opening 67 provided at the counter electrode 65, and reacts with the primary ions to be ionized. Such a method of generating primary ions using corona discharge in the air and ionizing a chemical substance in gas through a chemical reaction between the primary ions and the gas is called atmospheric pressure chemical ionization.

There is a potential difference of about 1 kV between the counter electrode 65 and the first aperture electrode 64, and so ions move toward the first aperture electrode 64 and are taken to a differential pumping region 69 via a first aperture 68. Adiabatic expansion occurs at the differential pumping region 69, so that so-called clustering occurs where solvent molecules or the like adhere to ions. To suppress clustering, the first aperture electrode 64 and a second aperture electrode 70 are desirably heated by a heater or the like.

Ions of a sample generated by the atmospheric pressure chemical ionization are introduced to the mass spectrometer 25 via the first aperture 68 of the first aperture electrode 64, the differential pumping region 69 where air is exhausted by an exhaust system (not illustrated) and a second aperture 71 of the second aperture electrode 70. Air of the mass spectrometer 25 is exhausted by an exhaust system (not illustrated). The ion source 23 and the mass spectrometer 25 form one container.

Ions of a sample introduced to the mass spectrometer 25 are subjected to mass spectrometry by an ion-trap type mass spectrometer. The data analyzer 27 has values of mass-to-charge ratio set beforehand that are necessary to identify a single or a plurality of dangerous substances to be detected. An output signal of a detector of the mass spectrometer, relating to the mass-to-charge ratio that is necessary to identify dangerous substances to be detected, is sent to the data analyzer 27 continuously at predetermined time intervals as a result of the mass spectrometry of the ions of the sample for data processing. The data analyzer 27 has storage means to store, as a database, mass spectrometry data (values of the mass-to-charge ratio and relative intensity) necessary to identify a plurality of dangerous substances such as explosives and drugs and determination thresholds of signal intensity that are criteria to determine the identification of dangerous substances. The mass-to-charge ratio of a signal sent to the data analyzer 27 is checked against the database read from the storage means. When it is identified as the mass-to-charge ratio stored for a certain dangerous substance and the intensity of the signal sent is larger than the determination threshold, the possibility of existence of such a dangerous substance is displayed at the operation panel 7 to inform the operator of as such.

Figure 11:
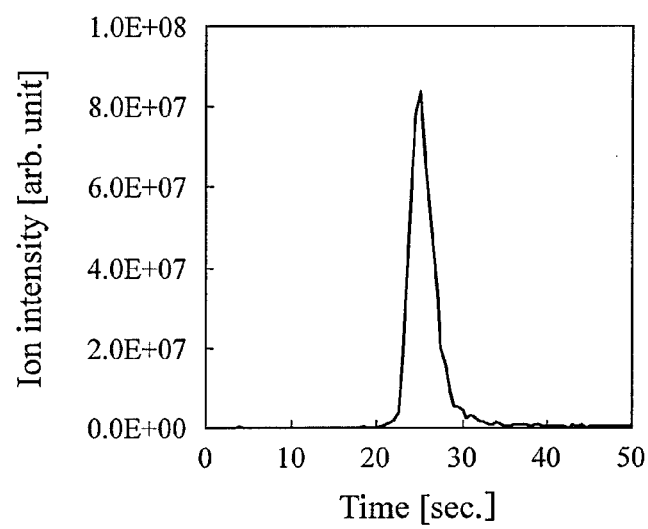
FIG. 11 shows a change over time in signal intensity of C4 explosive components detected from the baggage.

FIG. 11 shows a result of the inspection of baggage, to which C4 explosive particles are attached, using the trace detecting system of the present embodiment. The vertical axis of FIG. 11 represents the signal intensity in arbitral unit and the horizontal axis thereof represents time in the units of seconds.

As shown in FIG. 11, a clear signal can be obtained, indicating the detection of C4 explosive components. This result proved that the trace detecting system of Embodiment 1 enables removal of C4 explosive particles from actual baggage, to which the C4 explosive particles are attached, using air jet, collection of them at the collection filter 17, vaporization at the heating block 58 and detection of the C4 explosive components by the mass spectrometer 25.

The trace detecting system 1 according to the present embodiment as stated above enables inspection as to whether sample microparticles attached to baggage contains or not dangerous substances such as explosives without touching the baggage, automatically and under constant conditions, and so inspection can be conducted promptly without a need of skillful inspectors and without damaging and contaminating the baggage.

Next, the following describes a method of self-cleaning of the trace detecting system of the present embodiment.

Figure 12:
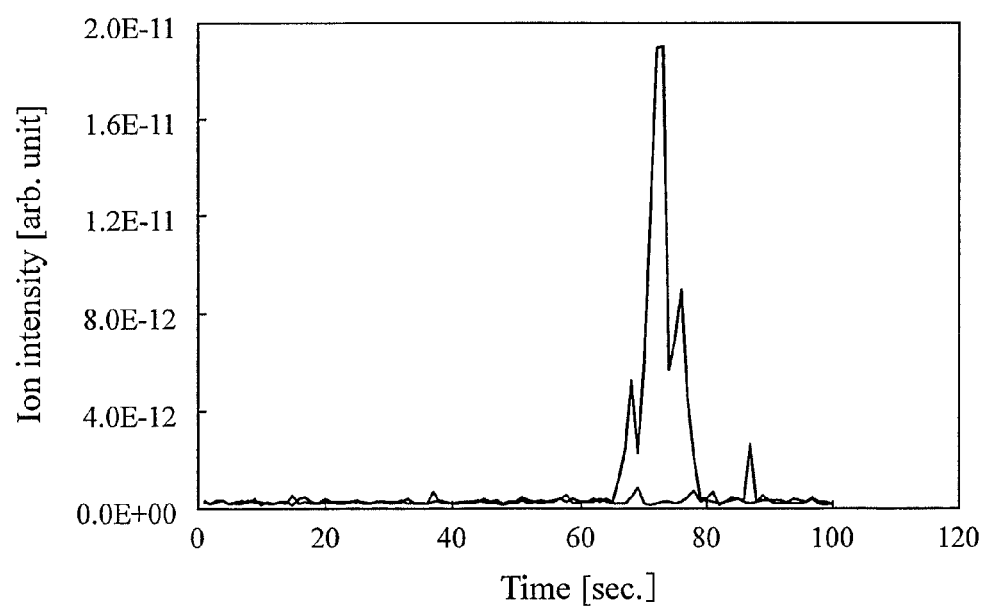
FIG. 12 shows a change over time in signal intensity of C4 explosive components detected from the sampling room after detecting the C4 explosive components therein.

FIG. 12 shows a result of examination of the presence or not of explosives at the collection filter 17 that is included at the trace detecting system 1 of the present embodiment, and is used when air jet is blown to the inner wall of the trace collector 43 after detection of C4 explosives there while sucking air by the exhauster 55. The vertical axis of FIG. 12 represents signal intensity in arbitral unit, and the horizontal axis thereof represents time in the units of seconds. As shown in FIG. 12, a signal indicating C4 explosives is clearly obtained from sample particles collected from the trace collector 43 after detection of C4 explosives there.

After detecting trinitrotoluene explosives by the trace detecting system 1 of the present embodiment, the present inventors examined the presence or not of the trinitrotoluene explosives collected at the collection filter 17 by blowing air jet to the inner wall of the L-shaped pipe 49 from the side of the connection with the coarse filter 45 while generating a cyclone phenomenon in the outer cylinder 57 by suction using the exhauster 55. The examination showed that the trinitrotoluene explosives were collected at the collection filter 17. It was found from this result that trinitrotoluene explosives particles remain inside of the L-shaped pipe 49 after collecting the trinitrotoluene explosives once.

Based on these results, the present inventors found that explosive microparticles remain at the trace collector 43 and the L-shaped pipe 49, once explosive microparticles are collected there. If the subsequent baggage is inspected in the state where dangerous microparticles such as explosive microparticles remain at the inner wall of the trace collector 43 and the L-shaped pipe 49, such dangerous microparticle remaining at the inner wall of the trace collector 43 and the L-shaped pipe 49 may be removed again, and be collected at the collection filter 17. In such a case, although such dangerous microparticles do not adhere to the baggage actually, such dangerous particles are detected erroneously, which becomes a factor of erroneous detection. In this way, the trace collector 43 and the L-shaped pipe 49 of the trace detecting system for baggage preferably has a self-cleaning function.

Possible cleaning means for the inner wall of the trace collector 43 and the L-shaped pipe 49 may be means to make an inspector wipe off the inner wall of the trace collector 43 carefully with a clean wiping member or means to replace the L-shaped pipe 49. However, considering the safety of the inspector, time required for cleaning or replacement, contamination by humans of the inner wall of the trace collector 43, they are not practical. In this way, the trace detecting system has to be equipped with an automatically cleaning function for the inner wall of the trace collector 43 and the L-shaped pipe 49.

The issues to be solved for the self-cleaning function include (1) a shorter possible duration for self-cleaning, enabling prompt resumption of the inspection, and (2) quantitative checking of the cleaning effect to prevent erroneous detections.

According to the trace detecting system 1 of the present embodiment, any special components and devices are not required for self-cleaning, and cleaning of the trace collector 43 can be performed automatically without humans in attendance, and the effect of cleaning can be checked quantitatively.

The self-cleaning by the trace detecting system 1 of the present embodiment is performed by the following procedure.

When the data analyzer 27 determines a result of the inspection as detection of explosive components, the operation panel 7 displays and informs the inspector of as such. Then, the trace detecting system 1 becomes a state of waiting for an instruction to start self-cleaning. When the inspector selects an instruction to execute self-cleaning via the operation panel 7, the central controller section 3 issues an instruction of a self-cleaning step to the trace collector controller 10 and the detector controller section 8.

The trace collector controller 10 stops normal inspection procedure and starts a predetermined self-cleaning step. The self-cleaning step is performed by the following procedure. The exhauster 55 is driven to suck the air in the trace collector 43, and the compressed gas generator 16 is driven.

Air jet at the pressure of 0.25 MPa is sprayed from the air nozzles nd, ne and nf (n denotes numerals 37, 38 and 39, the same applies to the following) of the first, second and third air nozzle groups 34, 35 and 36 in the sampling room 18 for 0.5 sec. After finishing the spraying of air jet from the air nozzles nd, ne and nf, air jet at the pressure of 0.25 MPa is sprayed from the nozzles nc and ng of the air nozzle groups 34, 35 and 36 for 0.5 sec. After finishing the spraying of air jet from the air nozzles nc and ng, air jet at the pressure of 0.25 MPa is sprayed from the nozzles nb and nh of the air nozzle groups 34, 35 and 36 for 0.5 sec. After finishing the spraying of air jet from the air nozzles nb and nh, air jet at the pressure of 0.25 MPa is sprayed from the nozzles na and ni of the air nozzle groups 34, 35 and 36 for 0.5 sec.

After finishing spraying of air jet in the sampling room 18, air jet at the pressure of 0.25 MPa is sprayed from the upper air nozzle group 50 of the trace collector 43 for 0.5 sec. After finishing spraying of air jet from the upper air nozzle group 50, air jet at the pressure of 0.25 MPa is sprayed from the lower air nozzle group 51 for 0.5 sec. After finishing spraying of air jet from the upper air nozzle group 50 and lower air nozzle group 51, air jet at the pressure of 0.25 MPa is sprayed from the assist air nozzle 54 of the L-shaped pipe 49 for 0.5 sec.

It has been demonstrated that the spraying of air jet to baggage can remove explosive microparticles from the baggage. Thus, explosive microparticles remaining in the sampling room 18, the trace collector 43 and the L-shaped pipe 49 can be removed by spraying air jet in the sampling room 18, the trace collector 43 and the L-shaped pipe 49, and can be conveyed to the separator section 12 by suction by the exhauster 55.

Next, self-inspection is performed as to whether the trace collector 43 and the L-shaped pipe 49 return to the cleanness similar to before the detection of explosive microparticles.

Every time air jet is sprayed for self-cleaning once, components detected from the collection filter 17 are compared with components of explosive microparticles stored beforehand. If the comparison shows that the trace detecting section 2 does not detect a signal of explosives, self-cleaning is finished, and normal inspection procedure is resumed. If it is determined at a level to detect a signal of explosives, self-cleaning is started again.

Figure 13:
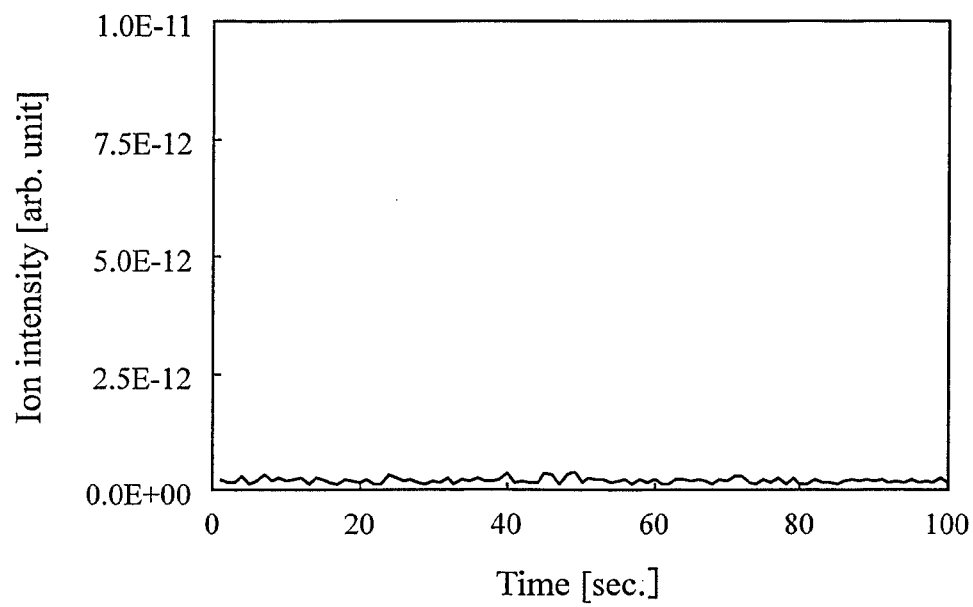
FIG. 13 shows a change over time in signal intensity after self-cleaning.

FIG. 13 shows a result of the inspection of the collection filter 17 that is used for self-cleaning of the trace detecting system 1 by the above method after the trace detecting system detects C4 explosives in the present embodiment.

FIG. 13 shows a result of the inspection after the aforementioned self-cleaning procedure is repeated eight times. As shown in FIG. 13, the self-cleaning procedure repeated eight times results in the state where a signal indicating C4 explosives does not change at all. This result shows that the self-cleaning method of the present embodiment can clear the trace detecting system 1.

The thus described self-cleaning means of the present embodiment can clean the trace collector 43 and the L-shaped pipe 49 of the trace detecting system 1 automatically and in a short time even after the system detects a dangerous substance such as explosives from baggage. Further, the trace detecting section 2 measures the cleanness of the trace collector 43 and the L-shaped pipe 49 after cleaning, and so the effect of cleaning can be checked quantitatively, which can prevent erroneous detections at the inspection following the detection of dangerous substances. Checking of the effect of self-cleaning does not have to be performed after every self-cleaning. The effect of self-cleaning may be checked after self-cleaning is finished a predetermined number of times, whereby time required for self-cleaning can be shortened. In this case, the stainless-steel coarse filter 46 of the coarse filter 45 may be replaced with a filter having coarseness with openings of 12.7 µm that is the same size of the collection filter 17, whereby dust discharged from the trace collector 43 during self-cleaning will not be conveyed to the collection filter 17, and so contamination of the separator section 12 and the ion source 23 can be prevented.

Next, the following describes an embodiment of the trace detecting system 1 that is configured to automatically replace the coarse filter 45 for self-cleaning.

Figure 14:
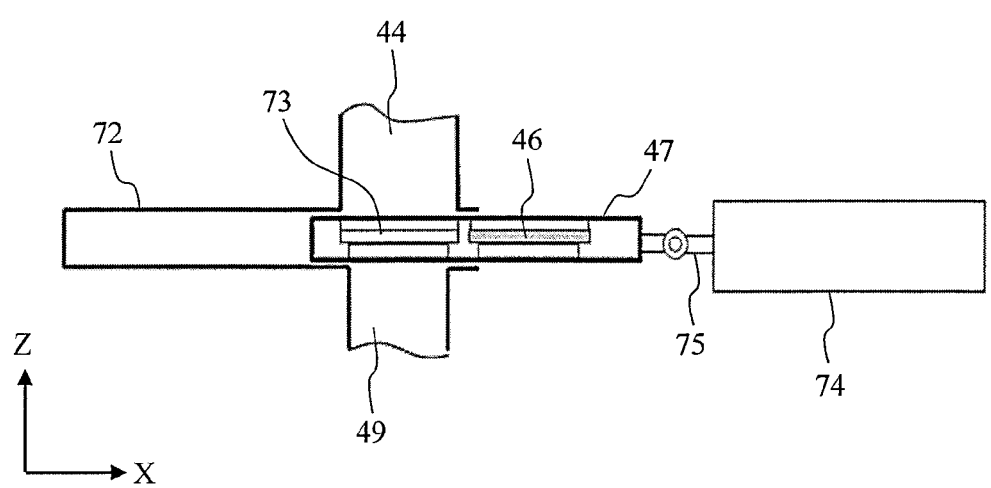
FIG. 14 explains an exemplary automatic replacement mechanism of a coarse filter.

FIG. 14 is a side view including a partial cross section to describe an automatic replacing section of the coarse filter 45. The side view of FIG. 14 is viewed from the positive direction of Y-axis, and omits the illustration of parts other than a replacement mechanism of the coarse filter 45.

The coarse filter 45 includes, in a coarse filter storage box 72, a stainless-steel coarse filter 46 having coarseness with openings of 0.2 mm and a fine mesh stainless steel filter 73 having coarseness with openings of 12.7 µm that are fixed in parallel on a tray 47. The tray 47 connects to a piston 75 of an air cylinder 74. When the compressed air is put into the air cylinder 74, then the piston 75 moves.

The following describes automatic replacement of the coarse filter 45 of the present embodiment.

When self-cleaning is selected at the trace detecting section 2, compressed air is firstly sent to the air cylinder 74 in the direction of pulling the piston 75 in. When the piston 75 is pulled in and then the tray 47 is drawn from the coarse filter storage box 72, the fine mesh stainless steel filter 73 having coarseness with openings of 12.7 µm moves to the position of the air inlet pipe 44. The position of the tray 47 is held by the air cylinder 74 during self-cleaning. After the aforementioned self-cleaning procedure is performed a predetermined number of times, compressed air is sent to the air cylinder 74 in the direction of pushing the piston 75 out. The tray 47 connecting to the piston 75 is pushed out together with the piston 75, and the coarse filter 46 having coarseness with openings of 0.2 mm returns to the position of the air inlet pipe 44. According to the present embodiment, the coarse filter 45 can be replaced automatically for self-cleaning, and so a more practical trace detecting system can be provided.

Next, the following describes an embodiment of the trace detecting system that is configured to enable successive inspections while replacing the collection filter 17 contaminated with dust or the like automatically.

It can be expected that the frequency of inspections of baggage performed per day may reach an enormous number depending on the place of inspections. Metals that are not vaporized when heated or a solid such as soil and sand typically adhere to baggage. When air jet is applied to such baggage, such a not-vaporized solid also will be removed from the baggage, and is collected at the collection filter 17. As the inspection of baggage continues successively, such a solid will be piled up at the collection filter 17, thus causing clogging of the collection filter 17 or increasing the intensity of background signal of the trace detecting section 2 due to gas generated therefrom, which becomes a factor to degrade the detection sensitivity. To avoid this, the trace detecting system 1 may be provided with a collection filter automatic replacement mechanism to replace the collection filter 17 appropriately and automatically, whereby inspections can be performed successively without causing such problems.

Figure 15:
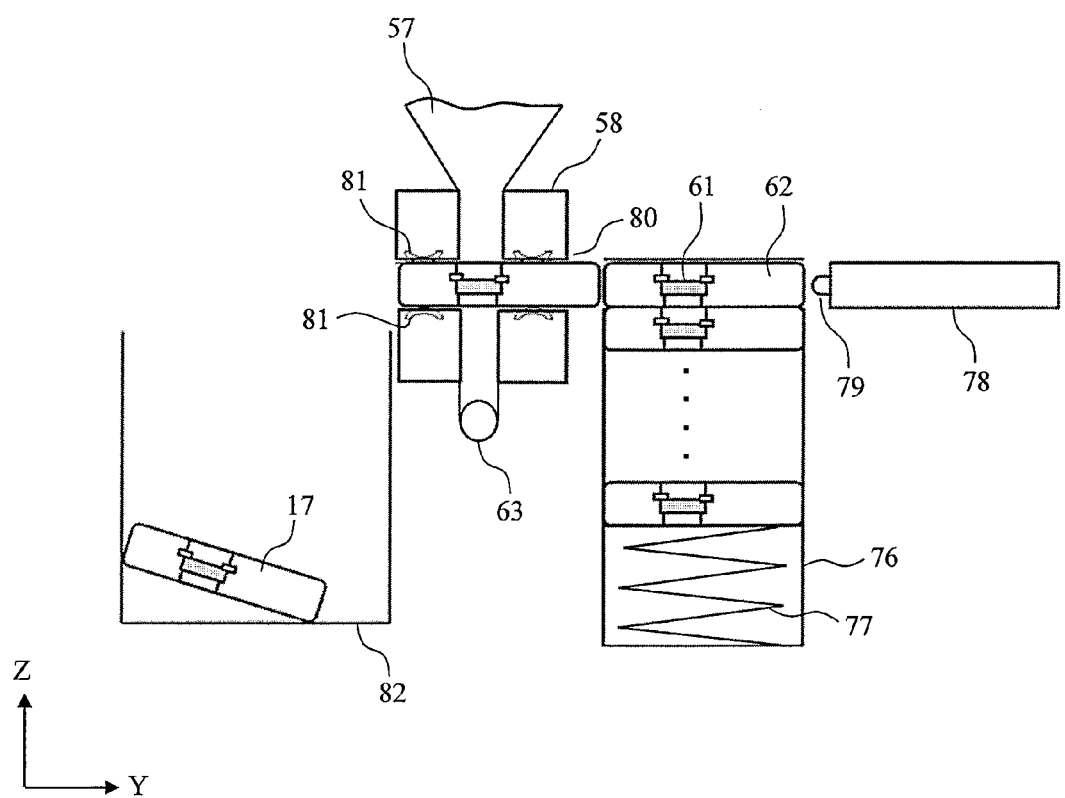
FIG. 15 explains an exemplary automatic replacement mechanism of a collection filter.

FIG. 15 is a front view including a partial cross section to describe the automatic replacement mechanism of the collection filter 17 in the trace detecting system. The front view of FIG. 15 is viewed from the negative direction of X-axis, and omits the illustration of parts other than the collection filter 17, the outer cylinder 57 and the heating block 58.

The automatic replacement mechanism of the collection filter 17 of the present embodiment includes ten collection filters 17 loaded in a storage box 76 in series. The storage box 76 is provided with a heater (not illustrated) and a thermometer (not illustrated), thus heating the collection filters 17 to the same temperature as the heating block 58 and keeping the temperature.

The storage box 76 is further provided with a spring 77 at its bottom face to always push the collection filters 17 against the top face of the storage box 76. The storage box 76 includes an air cylinder 78 to insert a collection filter 17 to the heating block 58. When compressed air is put into the air cylinder 78, a piston 79 moves.

The heating block 58 and the storage box 76 are provided with a through hole 80 to let a collection filter 17 pass therethrough. The through hole 80 of the heating block 58 includes a plate spring 81 stored therein, and when a collection filter 17 is inserted into the through hole 80 of the heating block 58, the collection filter 17 is held at the heating block 58 by a counterforce of the plate spring 81. At a position across the heating block 58 from the air cylinder 78, a used filter box 82 is provided to collect a collection filter 17.

The following describes automatic replacement of the collection filter 17 of the present embodiment.

When the signal intensity as background of the ion source detecting section 2 that is measured in the normal inspection mode exceeds a threshold value to determine the replacement of the collection filter 17, the operation panel 7 displays a message to urge the replacement of collection filter 17, and the system becomes a state of waiting for an instruction from the inspector. The inspection continues during that time as well. When the inspector selects the replacement of collection filter 17, the normal inspection mode ends, and a collection filter 17 replacement mode is executed. When the collection filter 17 replacement mode is executed, compressed air is sent to the air cylinder 78 in the direction of pushing out the piston 79. Then the piston 79 is pushed out until it comes into contact with the collection filter 17 in the storage box 76, and then pushes the collection filter 17 out from the storage box 76 and pushes it into the hole of the heating block 58. Then the contaminated collection filter 17 is pushed out by a new collection filter 17 from the heating block 58, and falls down into the used filter box 82. When the piston 79 is stretched fully, the new collection filter 17 moves to the position where the part of the stainless steel filter 61 thereof is located coaxially with the outer cylinder 57, and the collection filter 17 is held at the position by the plate spring 81 in the heating block 58. Next, compressed air is sent to the air cylinder 78 in the direction of pulling in the piston 79. The piston 79 is pulled in from the heating block 58 and the storage box 76, and returns to the standby position. Concurrently with the removal of the piston 79 from the storage box 76, a new collection filter 17 moves upward by the spring 77. The collected contaminated collection filter 17 is washed again or is replaced for reuse.

When the replacement of the collection filter 17 ends, the operation panel 7 displays a message of "ready to start inspection", and becomes a state of waiting for an instruction from the inspector. When the inspector issues an instruction to start inspection, then the system returns to the normal inspection mode.

According to the trace detecting system including an automatic replacement mechanism of the collection filter 17 as stated above, the contamination state of the collection filter 17 can be monitored quantitatively, and if it exceeds a threshold value to determine the replacement of the collection filter, the trace detecting system 1 can replace the collection filter 17 automatically. A new collection filter 17 for replacement can be heated to the same temperature as that of the heating block 58 beforehand and the temperature can be kept, and so it can eliminate the step of heating and degassing the collection filter 17 after replacement, and so can shorten the time to heat the collection filter 17 to the same temperature as that of the heating block 58 after inserting it into the heating block 58. As a result, the system can return to the normal inspection mode in a very short time after replacement of the collection filter 17, and so baggage can be inspected successively.

Figure 16:
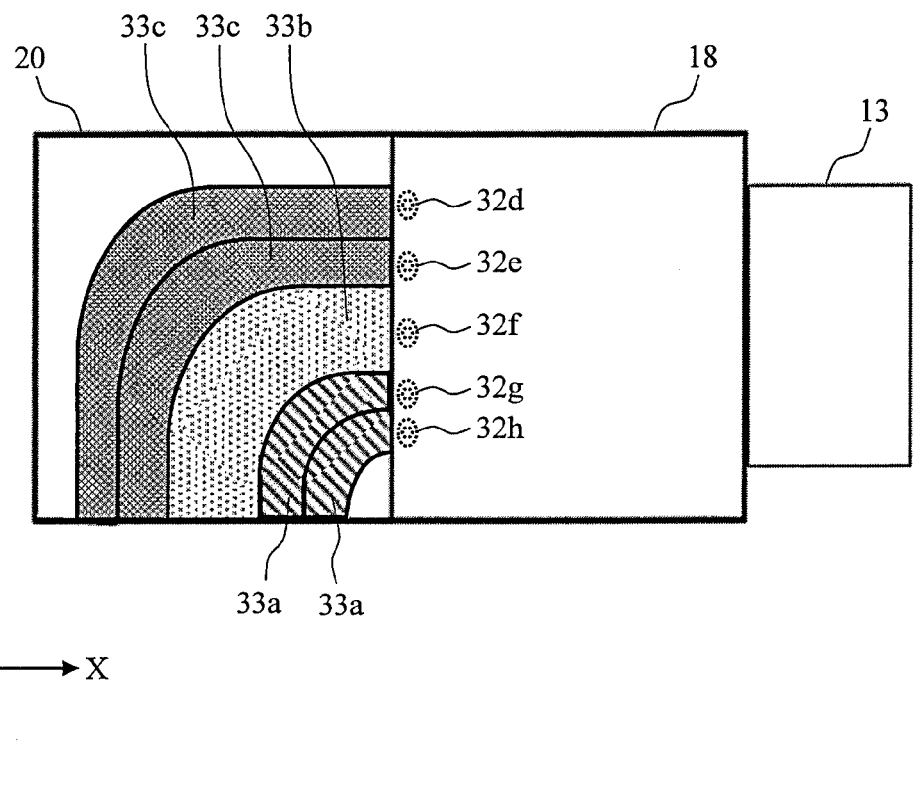
FIG. 16 shows other exemplary lanes to guide baggage to the sampling room.

FIG. 16 shows another embodiment of the trace detecting system including lanes, through which baggage 30 is inserted to the sampling room 18 depending on its type, a lane for some type of baggage 30 is brought closer to one side of the sampling room 18. FIG. 16 is a view from the positive direction of Z-axis and is a top view showing the appearance of the trace detecting system 1.

When small items and the like are inserted into the sampling room 18 at its central part under the conditions shown in FIG. 7 for inspection, a distance between the surface of small items and the respective air nozzles is large, and it becomes difficult to blow air jet at the air velocity of about 15 m/s to the surface of the small items in some cases. To solve this problem, the present embodiment is to place some type of baggage depending on their sizes at a position closer to one side of the sampling room 18 from the center thereof for insertion. The present embodiment allows small items to be inspected to be easily blown with air jet at 15 m/s or more.

The lanes are painted in three-different colors at the surface of the conveyor driver section 13 and the preparation table 20 at a position where the inspector can view. A blue lane 33a shows the range, through which small items are to be inserted into the sampling room 18, and guides the baggage to a position closer to a lower side of the drawing (on the side of the inspector) from the center of the sampling room 18. Similarly, a green lane 33b shows the range, through which relatively medium sized baggage such as handbags is to be inserted into the sampling room 18, and a red lane 33c shows the range, through which large-sized baggage such as trolley bags is to be inserted into the sampling room 18.

Insertion of baggage while bringing it closer to one side of the sampling room 18 decreases a distance between the air nozzles disposed at the inner side face of the sampling room 18 on the one side and the baggage, and so the baggage 30 can be effectively blown with air jet at smaller pressure and at the air velocity of about 15 m/s.

FIG. 17 shows the relationships among the output conditions of signals from the receivers 32a to 32h of the baggage detector 14, the air nozzles to be used and pressure of air jet sprayed from the air nozzles, which are based on the result of FIG. 6.

In FIG. 17, the receivers 32a to 32h of the baggage detector 14 that are listed on the left column indicate that light is blocked at these receivers and so the receivers are outputting signals. In letters listed on the upper column, na, nb, nc, nd, ne, nf, ng, nh and ni, n denotes numeral 37, 38 or 39. Oblique lines in the table of FIG. 17 indicate air nozzles that are not used in the corresponding conditions. Values of pressure for air jet listed in the table of FIG. 17 indicate the values of pressure that enable the application of air jet at the air velocity of about 20 m/s to the surface of the baggage 30 having an intermediate size between the maximum size and the minimum size that is found from the signal outputs of the baggage detector 14, and the unit of the values is MPa. Timing of air jet spraying from the air nozzles follows FIG. 8.

In the case of the smallest baggage for inspection, for example, the baggage detector 14 of the present embodiment outputs signals of the receivers 32a and 32h only. When this baggage enters the sampling room 18, air nozzles to spray air jet used are nozzles na, nb and nd of each air nozzle group 34, 35 and 36, and the other air nozzles are not used. The pressure of air jet sprayed is 0.05 MPa from the air nozzle na, 0.15 MPa from the air nozzle nb and 0.25 MPa from the air nozzle nd.

The present embodiment allows small baggage such as wallets to be blown with air jet at the air velocity of about 15 m/s or more effectively, and so trace detection can be performed more reliably.

Both of the conditions shown in FIG. 7 and FIG. 17 may be stored in the trace collector controller 10, whereby air jet can be applied effectively to the surface of baggage even when the baggage is conveyed to any position in the sampling room 18, so that it is more practical.

When both of the conditions shown in FIGS. 7 and 17 do not hold for the baggage, spraying conditions are set while referring to the outputs of the receivers 32a, 32b and 32c only of the baggage detector 14. FIG. 18 shows the relationships among the output conditions of signals from the receivers 32a, 32b and 32c of the baggage detector 14, the air nozzles to be used and pressure of air jet sprayed from the air nozzles.

In FIG. 18, the receivers 32 of the baggage detector 14 that are listed on the left column indicate that such receivers 32 are outputting signals. In letters listed on the upper column, na, nb, nc, nd, ne, nf, ng, nh and ni of FIG. 18, n denotes numeral 37, 38 or 39. Oblique lines in the table of FIG. 18 indicate air nozzles that are not used in the corresponding conditions. Values of pressure for air jet listed in the table of FIG. 18 indicate the values of pressure that enable the application of air jet at the air velocity of about 20 m/s to the surface of the baggage having an intermediate size between the maximum size and the minimum size that is found from the signal outputs of the baggage detector 14, and the unit of the values is MPa. Timing of air jet spraying from the air nozzles follows FIG. 8.

According to the present embodiment, air jet is sprayed while referring to the size of the baggage in the vertical direction only, and so air jet at about 15 m/s or more can be blown to the baggage having an indefinite shape as well effectively. This enables more reliable and practical trace detection.

For both of the conditions of FIG. 7 and FIG. 17, pressure of air jet sprayed may be made constant, and nozzles for spraying only may be selected for air-jet spraying. In this case, pressure of air jet is set at the highest pressure of 0.25 MPa for both of the conditions shown in FIG. 7 and FIG. 17. Since the present embodiment can eliminate the necessity to adjust the pressure of compressed air by the air nozzle controller 15, and so this can implement a trace detecting system at lower cost.

Figure 19:
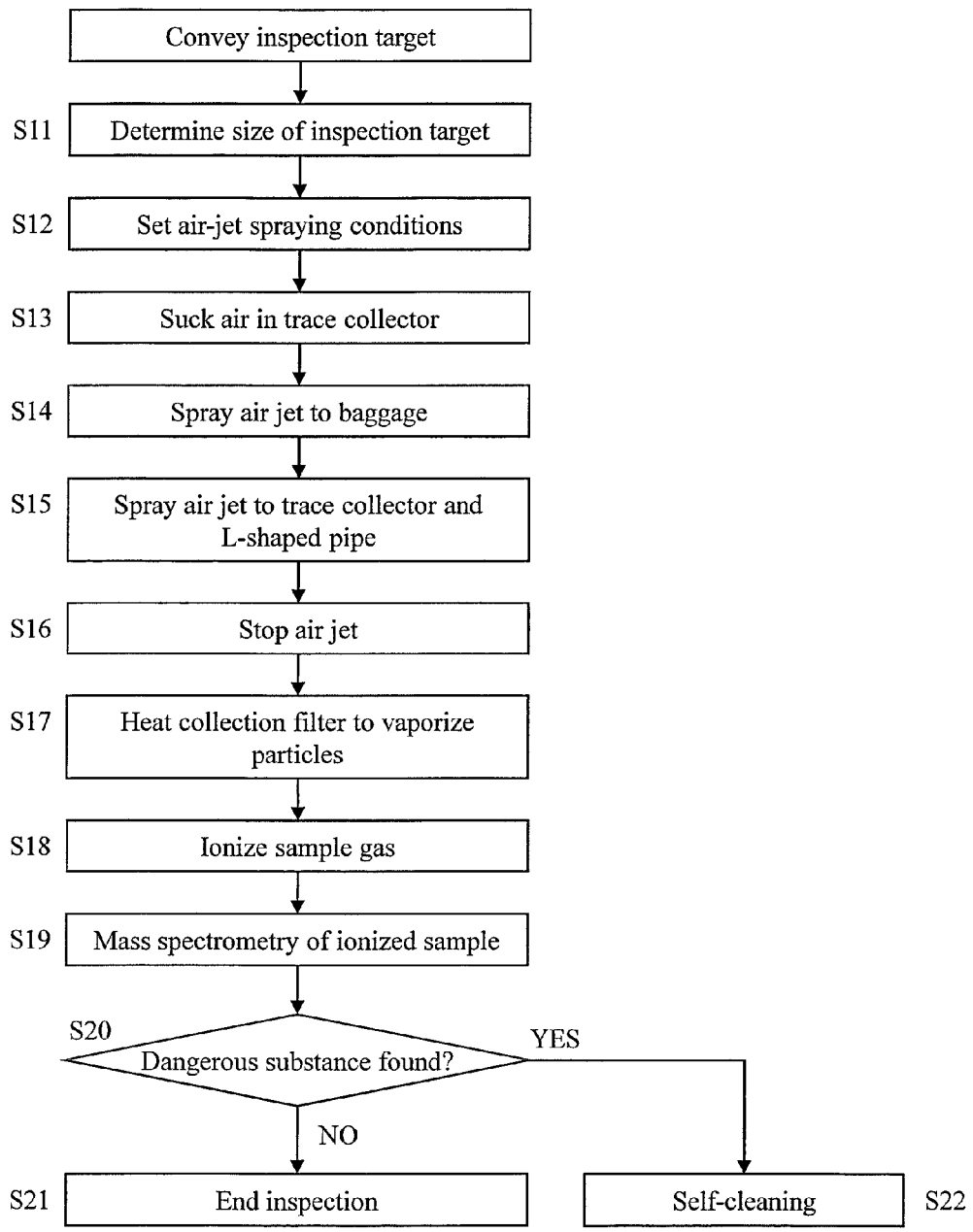
FIG. 19 is a flowchart to describe normal detection procedure.
Figure 20:
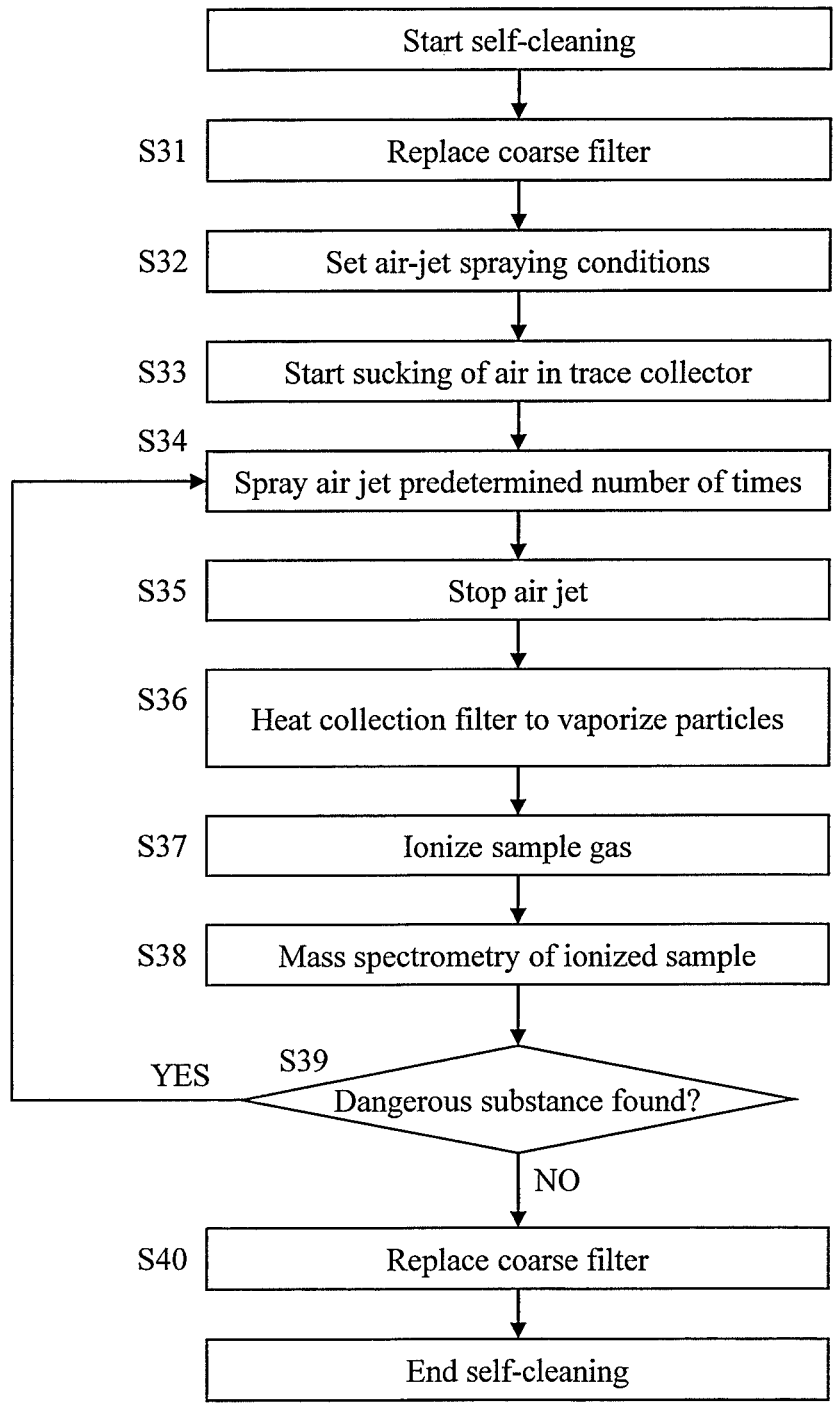
FIG. 20 is a flowchart to describe self-cleaning procedure.

Referring to FIGS. 19 and 20, the following describes the steps of baggage inspection and the steps of self-cleaning of the present embodiment as stated above.

FIG. 19 is a flowchart showing the steps of operations of various parts. Firstly, the following describes normal inspection steps.

When baggage 30 is conveyed, the size of the baggage 30 is firstly measured (S11), and spraying conditions are set at air nozzles of each air nozzle group 34, 35, 36 (S12). The spraying conditions are set by applying spraying patterns stored in the trace collector controller 10 as in FIG. 7, FIG. 17 and FIG. 18 to an electropneumatic regulator disposed at the air nozzle controller 15. Next, the exhauster 55 is driven to suck air in the trace collector 43 (S13), and then air jet is sprayed to the surface of the baggage 30 from an upper part to a lower part (S14). Spraying of air jet on a time-series basis is performed in accordance with the time sequence shown in FIG. 8. Next, air jet is sprayed from the upper air nozzle group 50 of the trace collector 43 and the assist air nozzle 54 of the L-shaped pipe 49 (S15). Then, air jet spraying from the air nozzles is stopped (S16).

Since the collection filter 17 is heated, sample microparticles captured at the collection filter 17 also are heated and so vaporized, thus generating sample gas (S17). The sample gas is conveyed to the ion source 23 and is ionized (S18), and then is conveyed to the mass spectrometer 25 for mass spectrometry (S19). Based on the result of analysis, the data analyzer 27 determines presence or not of any dangerous substance, and if any dangerous substance exits, the data analyzer identifies the type (S20). When no dangerous substances are detected as a result of the determination, inspection on the baggage ends (S21), and the inspection shifts to the next baggage. If any dangerous substance is detected as a result of the determination, the inspector is informed of the detection of the dangerous substance, and the system waits for an instruction whether or not to perform self-cleaning (S22).

Next, the following describes the steps of self-cleaning. FIG. 20 is a flowchart showing the steps of self-cleaning.

When the inspector issues an instruction for self-cleaning starting, the coarse filter 45 is replaced with a filter having coarseness with openings of 12.7 μm that is the same as of the collection filter 17 (S31). Concurrently spraying conditions of self-cleaning are transmitted to the air nozzle controller 15 and pressure of compressed air is adjusted (S32). The exhauster 55 is driven to suck air in the trace collector 43 (S33), and then air jet is sprayed from each air nozzle group 34, 35, 36, the upper air nozzle group 50 and the lower air nozzle group 51 of the trace collector 43 and the assist air nozzle 54 of the L-shaped pipe 49 (S34). This operation is performed a predetermined number of times, and then air jet spraying is stopped (S35). Steps 31 to 33 may be changed in their order or may be performed concurrently.

Then, sample microparticles captured at the collection filter 17 are analyzed. Specifically, the collection filter 17 is heated to vaporize the captured sample microparticles (S36), and the vaporized sample gas is ionized (S37). The ionized sample is then subjected to mass spectrometry by the mass spectrometer 25 (S38). Based on the result of analysis, the data analyzer 27 determines presence or not of any dangerous substance (S39). If no dangerous substances are detected, self-cleaning ends. Then the coarse filter 45 is replaced with the stainless-steel coarse filter 46 having coarseness with openings of 0.2 mm (S40), and the inspector is informed that the system is ready for normal inspection procedure. If any dangerous substance is detected, the procedure returns to Step 34, and the self-cleaning steps are repeated.

In this way, the present embodiment provides a trace detecting system enabling self-cleaning and such a trace detecting method. Since a collection filter can be replaced automatically, the present embodiment further provides a trace detecting system as well as a method that can improve the rate of operation and can reduce the number of persons required for inspection.

[Embodiment 2]

In the aforementioned embodiment, the air nozzles are disposed so that the air nozzles belonging to each air nozzle groups 34, 35, 36 are shifted each other by 5 cm in the baggage conveyance direction. Instead, the air nozzles belonging to each air nozzle groups 34, 35, 36 may be disposed in a line in the vertical direction without shifting them in the baggage conveyance direction.

Figure 21:
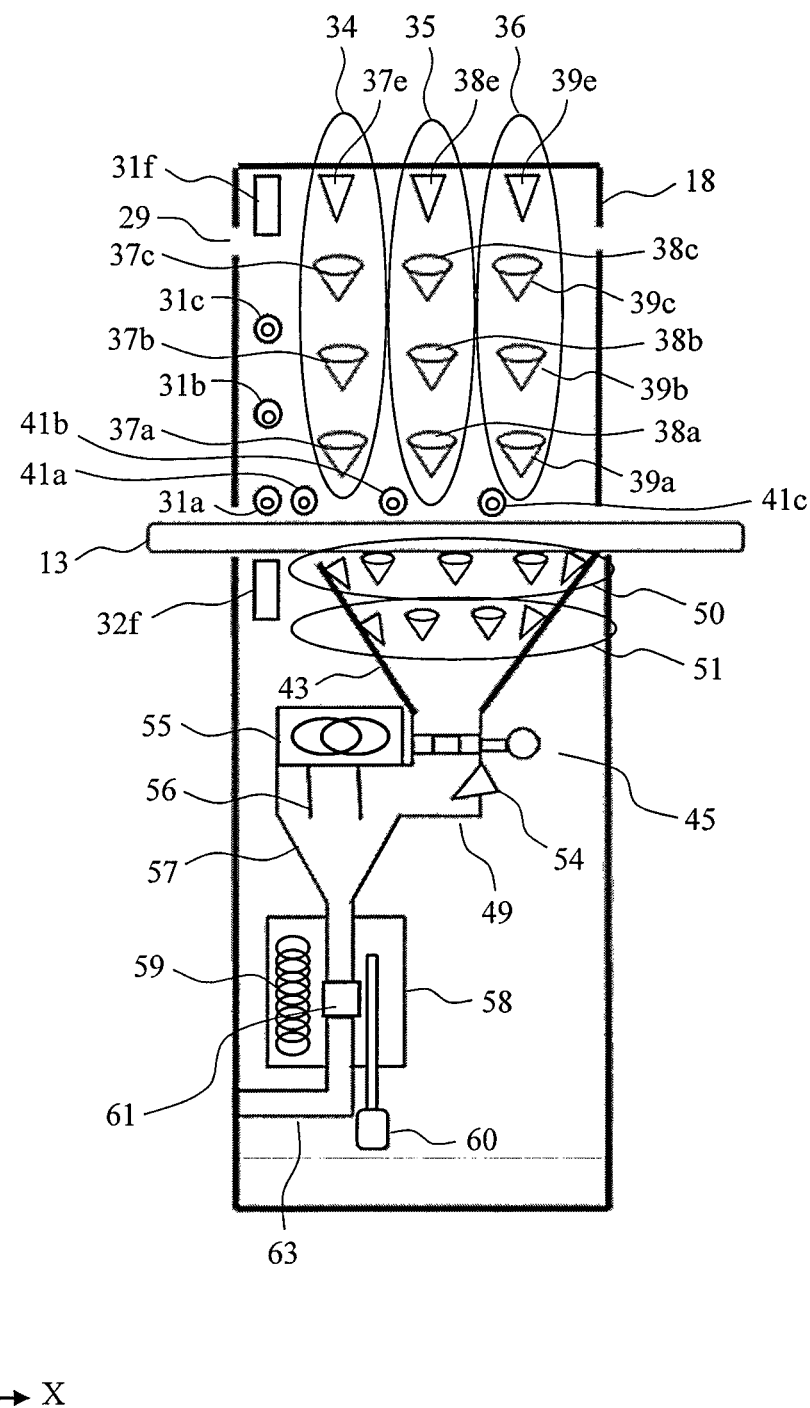
FIG. 21 explains an exemplary trace detecting system including different arrangement of air nozzle groups.

FIG. 21 shows an embodiment of the trace detecting system 1 including the air nozzle groups 34, 35 and 36 each being placed in a line in the vertical direction and placed in three lines in total. FIG. 21 describes the configuration of a baggage detector 14 and each air nozzle group 34, 35, 36 of the trace detecting system, and is a side view including a partial cross section in a sampling room 18. The cross-section of FIG. 21 is a section that passes through the center of the sampling room 18 and is parallel to the baggage conveyance direction of the sampling room 18. The side view is viewed from the positive direction of Y-axis, and omits the illustration of parts of a trace detecting section 2 other than a separator section 12 and a heating unit 22.

Figure 22:
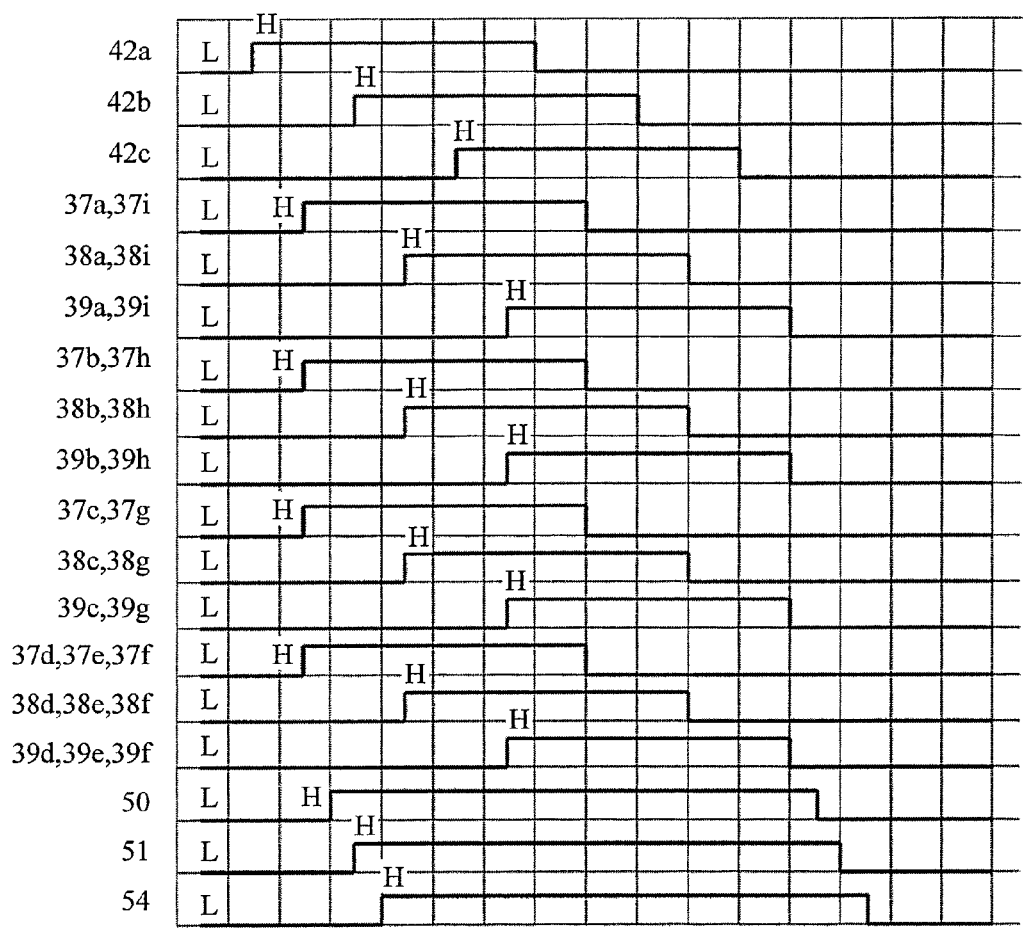
FIG. 22 is a timing chart showing spraying timings of air nozzles.

In FIG. 21, air nozzles 37a, 37b, 37c, 37d, 37e, 37f, 37g, 37h and 37i (the drawing shows the air nozzles 37a, 37b, 37c and 37e only) making up the first air nozzle group 34 are disposed in a vertical line at positions of the same X coordinate away from the sampling room entry 29 by 5 cm. Air nozzles 38a to 38i (the drawing shows the air nozzle 38a, 38b, 38c and 38e only) making up the second air nozzle group 35 are disposed in series at positions of the same X coordinate away from the first air nozzle group 34 by 5 cm. Air nozzles 39a to 39i (the drawing shows the air nozzle 39a, 39b, 39c and 39e only) making up the third air nozzle group 36 are disposed in a vertical line and in series at positions of the same X coordinate away from the second air nozzle group 35 by 5 cm. The trigger sensor 40 is disposed at the same position as that of Embodiment 1. FIG. 22 shows the spraying timings of air jet from the air nozzle groups 34, 35 and 36 according to the present embodiment.

When the receiver 42a of the trigger sensor outputs a signal, the air nozzles 37a to 37i making up the first air nozzle group 34 start spraying 0.2 sec. later. Similarly to Embodiment 1, during duration H when air jet is sprayed, the following spraying operation is repeated, i.e., air jet is sprayed for 0.1 sec., is stopped for 0.1 sec., and then is sprayed again for 0.1 sec. Air jet sprayed from the first air nozzle group 34 continues for 0.3 sec. after the signal output from the receiver 42a of the trigger sensor becomes off. Since the distance between the transmitter 41a of the trigger sensor and the first air nozzle group 34 is 5 cm, and it takes 0.25 sec. to pass through this distance because the conveyance speed is 12 m/min. In the present embodiment, the duration is set at 0.3 sec. to be on the safe side.

Following the receiver 42a of the trigger sensor, when the receiver 42b outputs a signal, the air nozzles 38a to 38i making up the second air nozzle group 35 start spraying of air jet. Similarly, when the receiver 42c of the trigger sensor outputs a signal, the air nozzles 39a to 39i making up the third air nozzle group 36 start spraying of air jet. Other timings of air jet spraying from the upper air nozzle group 50 and the lower air nozzle group 51 of the trace collector 43 and the assist air nozzle 54 of the L-shaped pipe 49 are the same as those of Embodiment 1.

Similarly to the case of the first air nozzle group 34, as for timings to stop the air jet spraying from the second air nozzle group 35 and the third air nozzle group 36, spraying continues for 0.3 sec. before ending after the signal output from the receiver 42b and the receiver 42c of the trigger sensor becomes off.

According to the present embodiment, since the air nozzles are disposed in series and in a line vertically, the length of depth of the sampling room 18 can be shortened. This leads to an advantageous effect of decreasing the footprint of the trace detecting system 1.

[Embodiment 3]

The trace detecting systems of Embodiment 1 and Embodiment 2 described above may be used in combination with an X-ray image diagnostic device, from which higher detection ability can be achieved.

The X-ray image diagnostic device typically has a very limited X-ray irradiation area to be irradiated with X-ray for imaging. Such an X-ray irradiation area typically is positioned near the center of the X-ray image diagnostic device. Then, at another position other than the X-ray irradiation area, the trace detecting means as described in Embodiments 1 and 2 can be incorporated.

Figure 23:
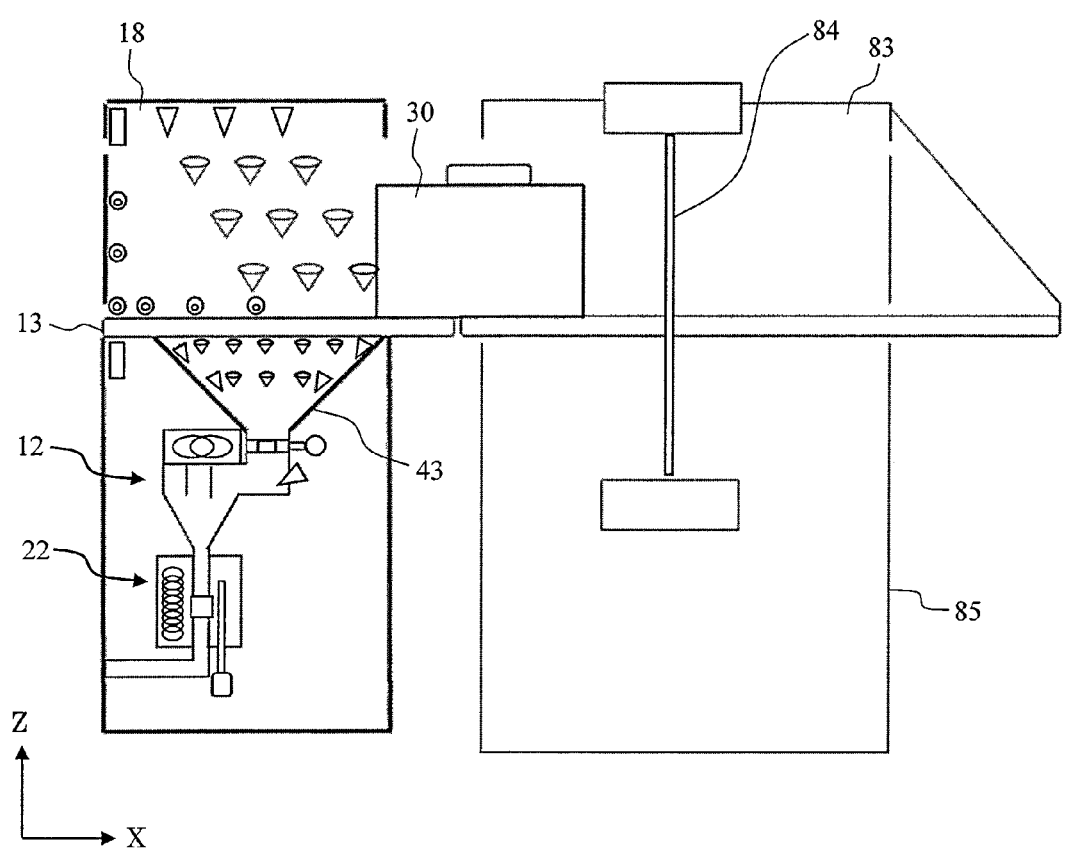
FIG. 23 shows a trace detecting system in combination with an X-ray diagnostic device.

FIG. 23 shows an embodiment including the combination of a conventional X-ray image diagnostic device 83 that is disposed in series with the trace detecting system 1 shown in Embodiment 1 or Embodiment 2. FIG. 23 is a side view that is viewed from positive direction of Y-axis, and omits the illustration of parts of the trace detecting section 2 other than the separator section 12 and the heating unit 22. The X-ray image diagnostic device 83 has an X-ray source in a mainframe 85, and an X-ray irradiation area 84 at the substantially center of the device. Simply by setting the conveyor driver section 13 of the trace detecting system 1 at the same height as that of the X-ray image diagnostic device 83, the baggage 30 can be inspected for trace detection and for inside by X-ray.

Figure 24:
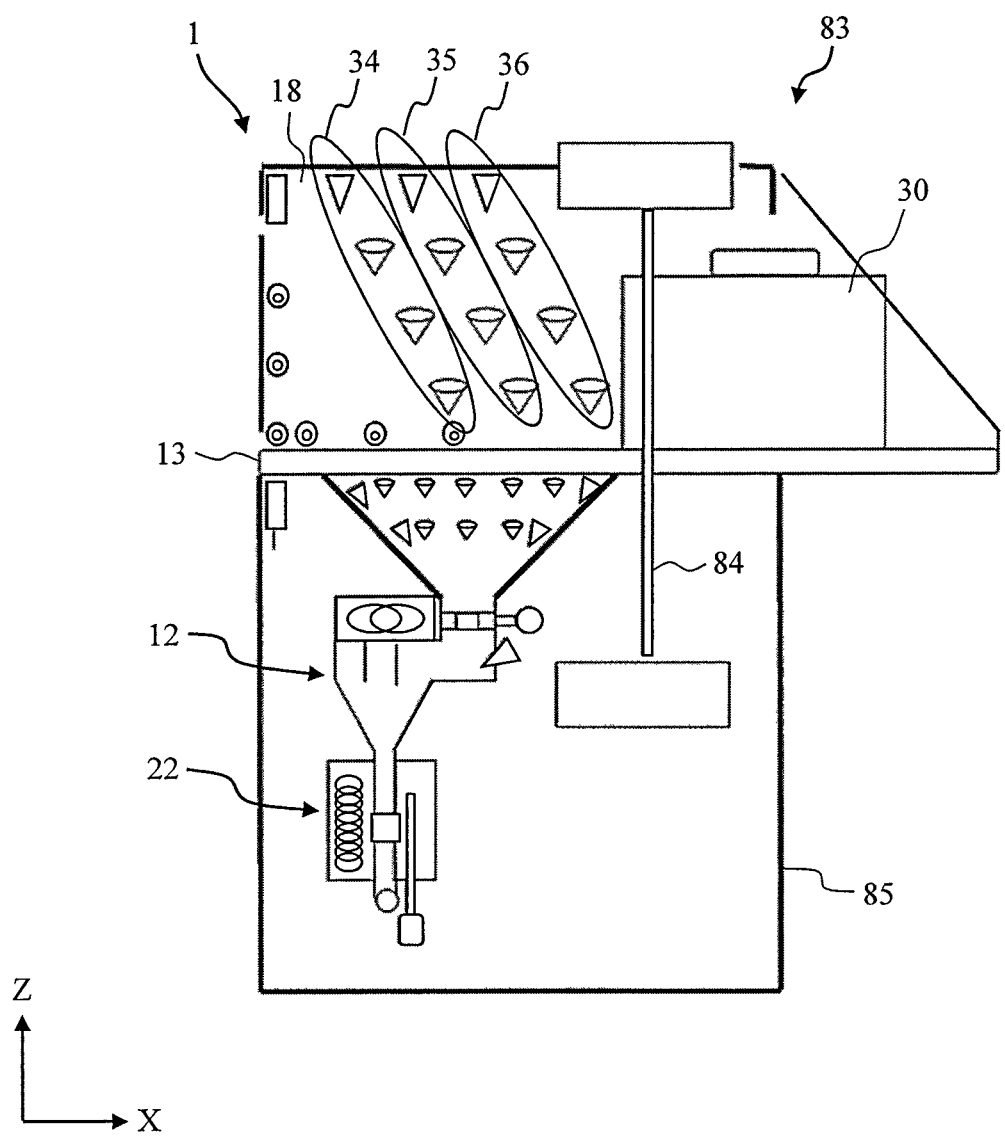
FIG. 24 shows an exemplary device of an X-ray diagnostic device internally including means for trace detecting.

FIG. 24 shows an embodiment of the X-ray image diagnostic device 83 including the means for trace detecting of the present invention therein in an integrated manner. FIG. 24 is a side view that is viewed from the positive direction of Y-axis, and omits the illustration of parts of the trace detecting section 2 other than the separator section 12 and the heating unit 22.

The present embodiment includes the X-ray image diagnostic device 83 for X-ray inspection that is disposed downstream of the air nozzle groups 34, 35 and 36. In the embodiment shown in FIG. 24, the ion source 23, the mass spectrometer 25, the detector controller section 8, the data analyzer 27, the suction pump 24 and the exhaust part 26 of the trace detecting section 2 shown in FIG. 2 are stored in the X-ray image diagnostic device mainframe 85, whereby the footprint of the device can be made smaller.

The embodiments of the trace detecting system 1 shown in FIG. 23 and FIG. 24 enable the inspection of sample microparticles attached to the baggage and the inspection of the inside of the baggage, and so reliability of the inspection can be improved.

[Embodiment 4]

The trace detecting systems of Embodiments 1 to 3 include three air nozzle groups, and they may include only one air nozzle group.

Figure 25:
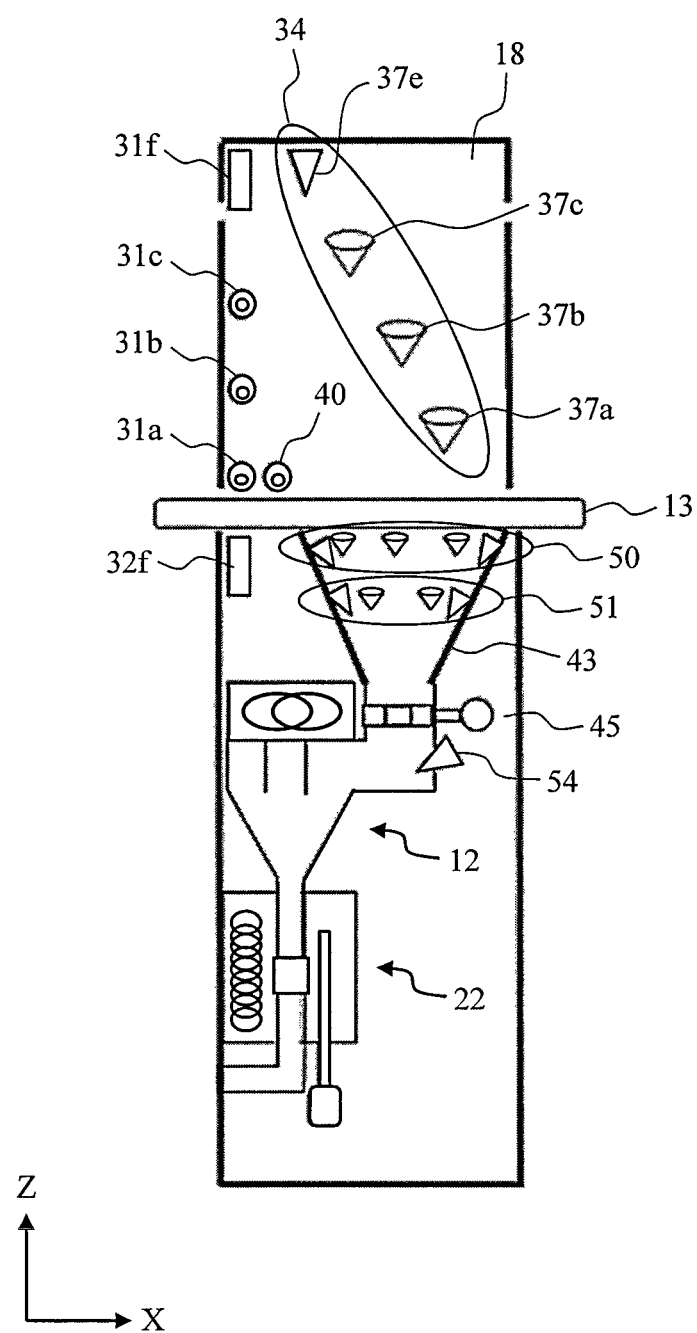
FIG. 25 shows an exemplary trace detecting system including one air nozzle group.

FIG. 25 shows an embodiment of the trace detecting system including only one air nozzle group 34. FIG. 25 is a side view including a partial cross section in a sampling room 18 to describe the configuration of the baggage detector 14 and the air nozzle group 34 of the trace detecting system. The cross-section of FIG. 25 is a section that passes through the center of the sampling room 18 and is parallel to the baggage conveyance direction of the sampling room 18. The side view of FIG. 25 is viewed from the positive direction of Y-axis, and omits the illustration of parts of a trace detecting section 2 other than a separator section 12 and a heating unit 22.

The trace detecting system of the present embodiment has the same configuration as that of Embodiment 1 except that it includes only one air nozzle group 34. Air nozzles 37a to 37i making up the air nozzle group 34 also are disposed similarly to Embodiment 1.

Figure 26:
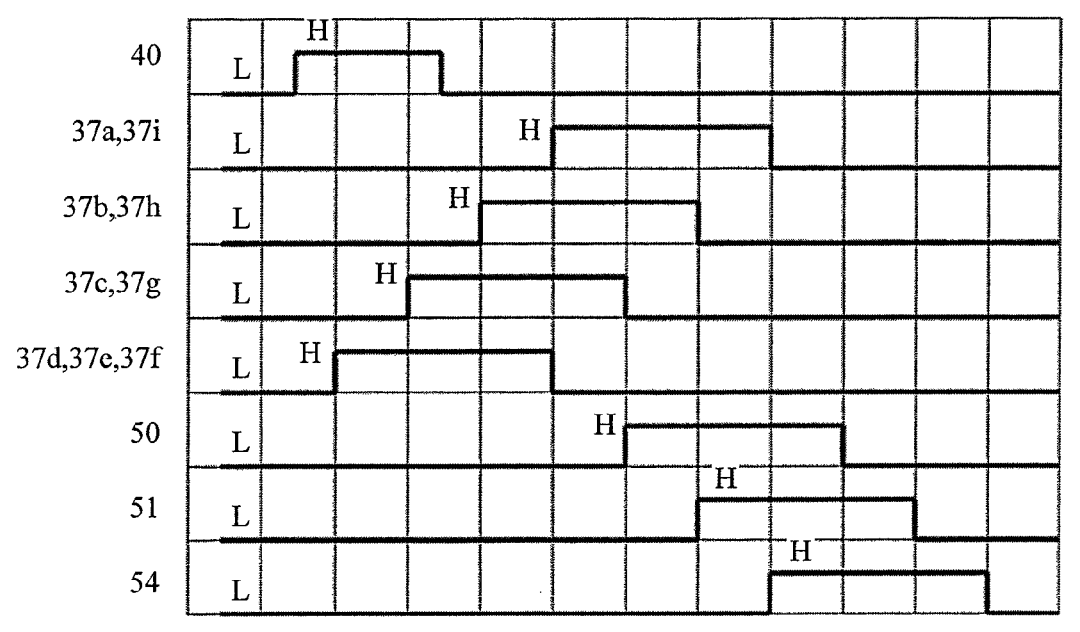

FIG. 26 shows timings of air jet spraying from the air nozzle group 34 of the present embodiment. When a pair of trigger sensor 40 provided at the sampling room entry 29 outputs a signal, then air jet is sprayed one by one from the nozzle 37d to the nozzle 37a. The spraying conditions are as shown in FIG. 7. When the signal output from the trigger sensor 40 becomes off, then the air jet spraying stops 0.3 sec. later one by one from the nozzles 37d to 37a. Since the present embodiment includes only one air nozzle group 34, the depth of the trace detecting system 1 can be made thin that is about ⅓ of the trace detecting system of Embodiment 1. Therefore, the trace detecting system of the present embodiment can be easily attached to the entry or the exit of the existing X-ray image diagnostic device 83.

Figure 27:
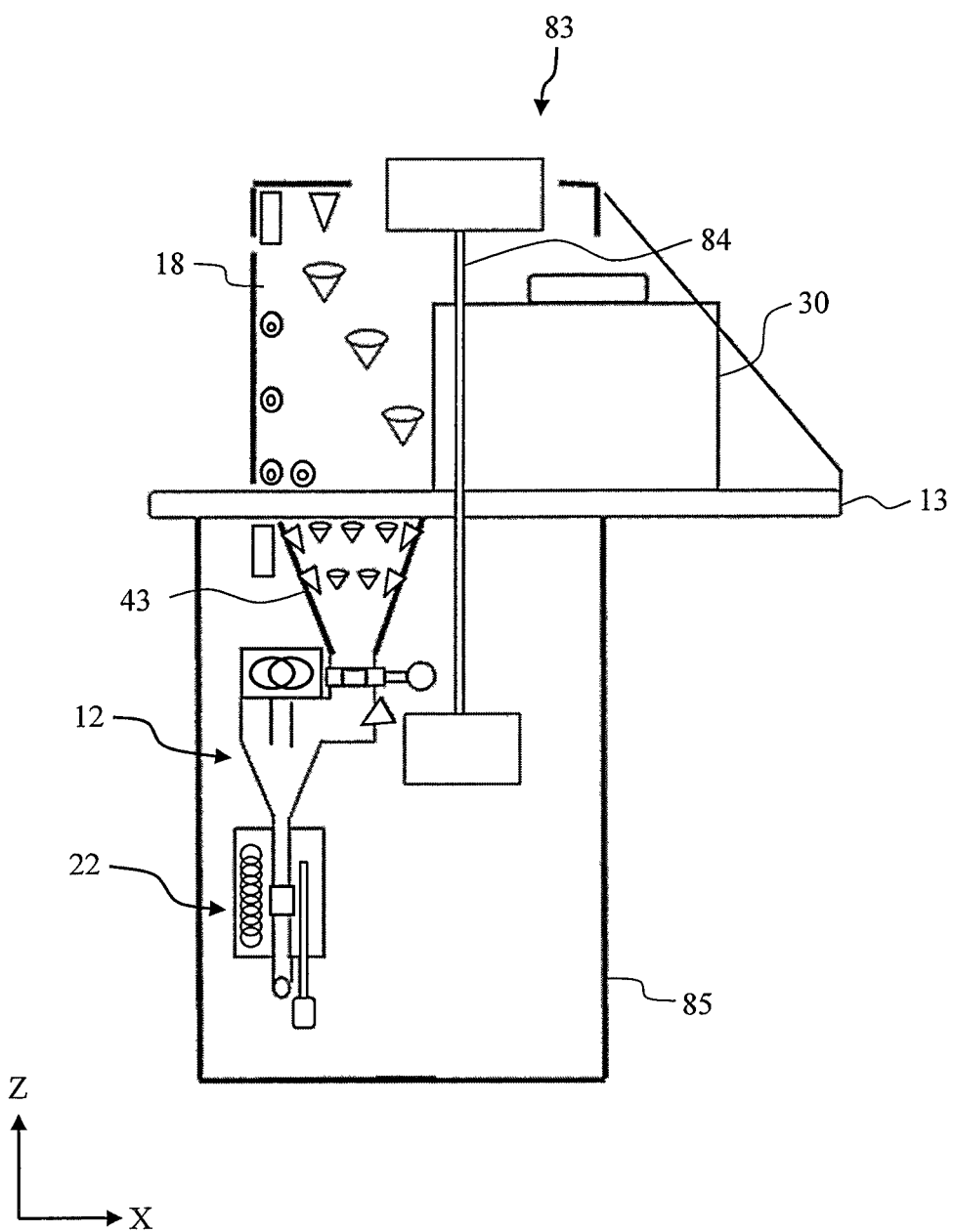
FIG. 27 shows an exemplary device including a trace detecting system assembled at an entry of an X-ray diagnostic device.

FIG. 27 shows an embodiment of the trace detecting system attached to the entry of the X-ray image diagnostic device 83. FIG. 27 is a side view that is viewed from the positive direction of Y-axis, and omits the illustration of parts of a trace detecting section 2 other than a separator section 12 and a heating unit 22.

In the embodiment shown in FIG. 27, the ion source 23, the mass spectrometer 25, the detector controller section 8, the data analyzer 27, the suction pump 24 and the exhaust part 26 of the trace detecting section 2 shown in FIG. 2 are stored in the X-ray image diagnostic device mainframe 85.

The present embodiment can modify the existing X-ray image diagnostic device 83 to a multifunctional detection device enabling bulk inspection by X-rays and trace detection at the same time without increasing the footprint of the device.

The trace detecting system of the present invention as described above is to inspect baggage having a size that can be carried onto an airplane as an inspection target. The range of inspection target can be broadened by changing the shape of insertion port of the sampling room. For instance, the entry of the sampling room can be made larger so as to deal with a large-sized suitcase that is checked baggage. The entry of the sampling room may have the same size as that of a human-body scanner using millimeter waves, whereby the operation in combination with the human-body scanner also is possible. The insertion port may have a size similar to that of the insertion port for mail of a mailbox, whereby inspection of mail, tickets such as boarding pass or the like can be inspected.

The aforementioned exemplary trace detecting systems of the present invention describe the configuration for automatic replacement of the coarse filter and the collection filter, and the inspector may replace them manually, from which the same effects of removing, collecting and detecting sample microparticles from baggage can be obtained, which is the object of the present invention. Similarly, the inspector may manually apply air jet while scanning the air jet over the surface of an inspection target so that the air jet at the air velocity of about 15 m/s or more can be applied to the surface of the inspection target, from which the same effects of removing, collecting and detecting sample microparticles from baggage can be obtained. In these cases, the trace detecting system does not have to include a baggage detector and a trigger sensor, and so a simple trace detecting system can be provided at lower cost.

The trace detecting systems of the present invention as stated above uses a cyclone phenomenon as means to separate sample microparticles and air flow. Instead, an impactor as a well-known technique may be used as the separation means, from which a similar effect to the present embodiment can be obtained.

The trace detecting system of the present invention as stated above includes mass-spectrometry means as the trace detecting section, and instead of the mass-spectrometry means, a trace detecting system that is of a well-known chemiluminescence type may be used in the present invention, which is to separate vapor of vaporized sample microparticles in an oven with a gas chromatograph and detect luminescent light that is a result of reaction of the vapors with a luminescent reagent, thus inspecting the presence or not of dangerous substances. Alternatively, a well-known ion-mobility type trace detecting system may be used in the present invention, which is to ionize the vapor with a radioisotope inside of the ion source, and then introduce it into a drift tube to detect the mobility of ions, thus inspecting the presence or not of dangerous substances.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

REFERENCE SIGNS LIST

1 Trace detecting system
2 Trace detecting section
3 Central controller section
4 Baggage conveyor section
5 Trace collector section
6 Power supply section
7 Operation panel
8 Detector controller section
9 Conveyor controller
10 Trace collector controller
11 Trace detecting system unit
12 Separator section
13 Conveyor driver section
14 Baggage detector
15 Air nozzle controller
16 Compressed gas generator
17 Collection filter
18 Sampling room
20 Preparation table
21 Pre-counter mainframe
22 Heating unit
23 Ion source
24 Suction pump
25 Mass spectrometer
26 Exhaust part
27 Data analyzer
28 Handle
29 Sampling room entry
30 Baggage
31 Transmitter
32 Receiver
33 Lane
34 First air nozzle group
35 Second air nozzle group
36 Third air nozzle group
37 Air nozzle
38 Air nozzle
39 Air nozzle
40 Trigger sensor
41 Transmitter
42 Receiver
43 Trace collector
44 Air inlet pipe
45 Coarse filter
46 Stainless steel coarse filter
47 Tray
48 Handle
49 L-shaped pipe
50 Upper air nozzle group
51 Lower air nozzle group
52 Upper air nozzle
53 Lower air nozzle
54 Assist air nozzle
55 Exhauster
56 Inner cylinder
57 Outer cylinder
58 Heating block
59 Heater
60 Thermometer
61 Stainless steel filter
62 Cartridge
63 Introducing pipe
64 First aperture electrode
65 Counter electrode
66 Needle electrode
67 Opening
68 First aperture
69 Differential pumping region
70 Second aperture electrode
71 Second aperture
72 Coarse filter storage box
73 Fine mesh stainless steel filter
74 Air cylinder
75 Piston 76 Storage box
77 Spring
78 Air cylinder
79 Piston
80 Through hole
81 Plate spring
82 Used filter box
83 X-ray image diagnostic device
84 X-ray irradiation area
85 X-ray image diagnostic device mainframe

The invention claimed is:

1. A trace detecting system comprising:
a removal section including a plurality of air nozzles fixed to an inner wall thereof to spray air jet from the air nozzles to an inspection target that is conveyed inside thereof and remove a sample substance attached to the inspection target;
a detection section to detect the removed sample substance;
conveyance means to convey the inspection target;
a size detection section to detect a size of the inspection target that is conveyed by the conveyance means; and
an air nozzle control section to control operations of the plurality of air nozzles, wherein the air nozzle control section selects an air nozzle capable of spraying air jet at 15 m/s or more to the surface of the inspection target from the plurality of air nozzles based on an output signal, received from the size detection section, comprising information about the size of the inspection target and makes the selected air nozzle spray air jet, wherein the air nozzle control section is configured to:
store first information on an air nozzle to be operated corresponding to an output signal from the size detection section and second information on pressure of compressed air to be supplied to the air nozzle to be operated, and
select, from a plurality of air nozzles, an air nozzle and adjust pressure therefor in accordance with the stored first and second information and information indicating pressure ranges at which each of the plurality of air nozzles is configured to spray air jet.

2. The trace detecting system according to claim 1, further comprising:
a separator section to separate sample microparticles from air including the sample substance; and
a conical shaped collector section to guide air including a sample substance from the removal section to the separator section, wherein the collector section includes a plurality of air nozzles at an inner face thereof to blow air jet.

3. The trace detecting system according to claim 2, wherein the separation section utilizes a cyclone phenomenon, the collector section and the separation section are jointed by a L-shaped pipe, and the L-shaped pipe includes a nozzle at an inner face thereof to blow air jet.

4. The trace detecting system according to claim 1, wherein the plurality of air nozzles of the removal section are disposed at a top face and both side faces of the inner wall of the removal section, and the air nozzle control section controls the plurality of air nozzles so that the air nozzles operate in the order from an upper part to a lower part.

5. The trace detecting system according to claim 1, wherein the conveyance means is provided with a mark on an upstream side thereof, the mark functioning as a criterion for an introduction position of the inspection target into the removal section in accordance with a size of the inspection target.

6. A method for trace detecting, comprising the steps of:
acquiring an outer-shape signal indicating an outer shape of an inspection target;
store first information on an air nozzle to be operated corresponding to an output signal from the size detection section and second information on pressure of compressed air to be supplied to the air nozzle to be operated;
referring to stored information related to the outer shape of the inspection target from the outer shape signal and selecting, based on the stored information related to the outer shape of the inspection target, the first information, the second information, and information indicating pressure ranges at which each of the plurality of air nozzles is configured to spray air jet, an air nozzle to be operated among a plurality of nozzles provided at a removal section and adjusting pressure therefor in accordance with the stored first and second information;
spraying air jet with controlled pressure from the selected air nozzle to an inspection target that is conveyed inside of the removal section;
collecting a sample substance and air removed from the inspection target by a conical shaped collector section and sending the same to a separator section;
separating the sample substance and air removed from the inspection target at the separator section;
vaporizing the separated sample substance to generate sample gas; and
inspecting the sample gas to identify the sample substance.

7. The method for trace detecting according to claim 6, further comprising the step of:
following the step of spraying air jet to the inspection target that is conveyed inside of the removal section, spraying air jet to an inner wall of the removal section and an inner wall of the collector section.

8. The method for trace detecting according to claim 6, further comprising the step of:
when the inspection shows that the sample substance is identified as a dangerous substance, spraying air jet to an inner wall of the removal section and an inner wall of the collector section for self-cleaning.

9. The method for trace detecting according to claim 8, further comprising the steps of:
after the self-cleaning, spraying air jet to the inner wall of the removal section and the inner wall of the collector section to separate sample microparticles from generated air flow;
vaporizing the separated sample substance to generate sample gas; inspecting the sample gas to identify the sample substance; and
when the inspection detects the dangerous substance, spraying air jet to the inner wall of the removal section and the inner wall of the collector section again for self-cleaning.

10. A trace detecting system comprising:
a removal section including a plurality of air nozzles fixed to an inner wall thereof to spray air jet from the air nozzles to an inspection target that is conveyed inside thereof and remove a sample substance attached to the inspection target;

a detection section to detect the removed sample substance; conveyance means to convey the inspection target;

a size detection section to detect a size of the inspection target that is conveyed by the conveyance means;

an air nozzle control section to control operations of the plurality of air nozzles, wherein the air nozzle control section selects an air nozzle capable of spraying air jet at 15 m/s or more to the surface of the inspection target based on an output signal from the size detection section, and makes the selected air nozzle spray air jet a separator section to separate sample microparticles from air including the sample substance; and a conical shaped collector section to guide air including a sample substance from the removal section to the separator section, wherein the collector section includes a plurality of air nozzles at an inner face thereof to blow air jet.

11. The trace detecting system according to claim 10, wherein the separation section utilizes a cyclone phenomenon, the collector section and the separation section are jointed by a L-shaped pipe, and the L-shaped pipe includes a nozzle at an inner face thereof to blow air jet.

* * * * *